US012789038B2

(12) United States Patent
Van Der Hoeven

(10) Patent No.: US 12,789,038 B2
(45) Date of Patent: Nov. 10, 2026

(54) INFRARED-INTEGRATED TRAINING

(71) Applicant: MAV-IP LLC, Irvine, CA (US)

(72) Inventor: Martin Arnold Van Der Hoeven, Irvine, CA (US)

( * ) Notice: Subject to any disclaimer, the term of this patent is extended or adjusted under 35 U.S.C. 154(b) by 36 days.

(21) Appl. No.: 19/090,339

(22) Filed: Mar. 25, 2025

(65) Prior Publication Data

US 2025/0303219 A1 Oct. 2, 2025

Related U.S. Application Data

(60) Provisional application No. 63/570,177, filed on Mar. 26, 2024.

(51) Int. Cl.
*A63B 21/00* (2006.01)
*A61N 5/06* (2006.01)
(Continued)

(52) U.S. Cl.
CPC ............ *A63B 21/4035* (2015.10); *A61N 5/06* (2013.01); *A63B 21/026* (2013.01); *A63B 21/04* (2013.01);
(Continued)

(58) Field of Classification Search
CPC .............. A61N 5/06; A61N 2005/0632; A61N 2005/0643; A61N 2005/0652; A61N 2005/0659; A61N 15/02; A61N 2201/10; A63B 21/00058; A63B 21/00065; A63B 21/026; A63B 21/04; A63B 21/0407; A63B 21/0435; A63B 21/0442; A63B 21/0552;
(Continued)

(56) References Cited

U.S. PATENT DOCUMENTS 217,918 A * 7/1879 White ................ A63B 21/0552 482/130
D317,959 S * 7/1991 Francis ........................ D21/673
(Continued)

FOREIGN PATENT DOCUMENTS

CN 213432839 U 6/2021
EP 0847779 A1 6/1998

OTHER PUBLICATIONS

International Search Report (ISA/US) for PCT/US2025/021398, mailed May 19, 2025.
(Continued)

*Primary Examiner* — Gary D Urbiel Goldner
(74) *Attorney, Agent, or Firm* — Chang & Hale LLP

(57) ABSTRACT

A multi-functional exercise system includes a base having a user-support top surface including a back-support portion being angled and positioned at a lateral center of the base and first and second foot platforms positioned on opposite lateral sides of the back-support portion. The base includes a headrest form positioned adjacent to the back-support portion of the base, an array of infrared (IR) lights including a first portion associated with the back-support portion of the base and a second portion associated with the headrest form, a first resistance band tube positioned on a first lateral side of the base, the first resistance band tube having a first resistance band segment disposed therein and a second resistance band tube positioned on a second lateral side of the base, the second resistance band tube having a second resistance band segment disposed therein.

13 Claims, 25 Drawing Sheets

(51) Int. Cl.

| | |
|---|---|
| ***A63B 21/02*** | (2006.01) |
| ***A63B 21/04*** | (2006.01) |
| ***A63B 21/055*** | (2006.01) |
| ***A63B 21/06*** | (2006.01) |
| ***A63B 21/072*** | (2006.01) |
| ***A63B 21/075*** | (2006.01) |

(52) U.S. Cl.
CPC ...... *A63B 21/0442* (2013.01); *A63B 21/0552* (2013.01); *A63B 21/0557* (2013.01); *A63B 21/0605* (2013.01); *A63B 21/0724* (2013.01); *A63B 21/075* (2013.01); *A63B 21/4033* (2015.10); *A61N 2005/0632* (2013.01); *A61N 2005/0643* (2013.01); *A61N 2005/0652* (2013.01); *A61N 2005/0659* (2013.01); *A63B 2213/002* (2013.01); *A63B 2225/10* (2013.01); *A63B 2225/74* (2020.08)

(58) Field of Classification Search
CPC ............ A63B 21/0557; A63B 21/0601; A63B 23/0233; A63B 23/03508; A63B 23/03516; A63B 23/0482; A63B 23/1236; A63B 23/1245; A63B 23/1281; A63B 2023/0411; A63B 2071/027; A63B 2208/0223; A63B 2208/0252; A63B 2213/00; A63B 2213/002; A63B 2225/10; A63B 2225/74
See application file for complete search history.

(56) References Cited

U.S. PATENT DOCUMENTS

| | | | | | |
|---|---|---|---|---|---|
| D392,004 | S * | 3/1998 | Van Der Hoeven | ......... | D21/673 |
| 5,935,050 | A * | 8/1999 | Shahan | .............. | A63B 21/4015 482/145 |
| 6,015,370 | A | 1/2000 | Pandozy | | |
| 6,752,745 | B1 * | 6/2004 | Davis | ................. | A63B 21/1609 482/130 |
| 8,672,817 | B2 * | 3/2014 | Bowser | ............ | A63B 23/03541 482/121 |
| 12,420,131 | B1 * | 9/2025 | Nayak | .................. | A63B 21/153 |
| 2007/0111869 | A1 * | 5/2007 | Wallach | ............. | A63B 21/4043 482/121 |
| 2010/0041526 | A1 | 2/2010 | Bowser et al. | | |
| 2010/0069801 | A1 * | 3/2010 | Tsai | ................... | A63B 21/0552 601/134 |
| 2018/0360649 | A1 | 12/2018 | Daffer | | |
| 2020/0069994 | A1 * | 3/2020 | Plumbar | ............ | A63B 21/0442 |
| 2021/0244960 | A1 | 8/2021 | Shanker | | |
| 2025/0303226 | A1 * | 10/2025 | Van Der Hoeven | ... | A61H 15/02 |

OTHER PUBLICATIONS

International Search Report and Written Opinion (ISA/US) for PCT/US2025/021398, mailed May 19, 2025.

* cited by examiner

INFRARED-INTEGRATED TRAINING

RELATED APPLICATION(S)

This application claims the benefit of U.S. Provisional Patent Application Ser. No. 63/570,177, filed on Mar. 26, 2024 and entitled INFRARED-INTEGRATED TRAINING, the complete disclosure of which is hereby incorporated by reference in its entirety.

BACKGROUND

In some implementations, the present disclosure relates to exercise/training systems and infrared (IR) lighting therapy systems. Many individuals seek ways to improve their physical health, manage stress, and recover from exercise or injury. As a result, various types of exercise equipment and therapeutic devices have been developed to assist users in building strength, enhancing flexibility, improving circulation, and accelerating recovery. These systems range from traditional resistance-training machines to passive therapy devices incorporating vibration, massage, or light-based modalities. IR light therapy has gained increasing attention for its potential therapeutic benefits. Studies have suggested that IR exposure can promote circulation, relax muscle tissue, reduce inflammation, and support post-exercise recovery. However, conventional IR therapy systems are designed solely for passive use, typically requiring the user to remain stationary while IR light is applied.

SUMMARY

Described herein are methods, systems, and devices relating to infrared-enhanced/integrated exercise, training, and therapy.

In some implementations, the present disclosure relates to a multi-functional exercise system comprising a base having a user-support top surface including an angled back-support portion positioned at a lateral center of the base and first and second foot platforms positioned on opposite lateral sides of the back-support portion. The system further comprises a headrest form positioned adjacent the back-support portion of the base, an array of infrared (IR) lights including a first portion associated with the back-support portion of the base and a second portion associated with the headrest form, a first resistance band tube positioned on a first lateral side of the base, the first resistance band tube having a first resistance band segment disposed at least partially therein and configured to extend out of a distal opening of the first resistance band tube, and a second resistance band tube positioned on a second lateral side of the base, the second resistance band tube having a second resistance band segment disposed at least partially therein and configured to extend out of a distal opening of the second resistance band tube.

The first and second resistance band tubes can be pivotably coupled to the base in a manner as to allow rotation of the first and second resistance band tubes between a stowed position at least partially substantially parallel with a bottom surface of the base and a raised position substantially perpendicular to the bottom surface of the base. In some examples, a distal end of the first resistance band segment has a grip handle associated therewith. The grip handle can have a base configured to support the grip handle on the distal opening of the first resistance band tube.

The system can further comprise a resistance bar attached at a first end to a distal end of the first resistance band segment and at a second end to a distal end of the second resistance band segment. For example, the resistance bar can include a first handle on a first lengthwise side of the resistance bar, a second handle on a second lengthwise side of the resistance bar, and a first compartment for placement of removable weights positioned between the first handle and the second handle. In some implementations, the resistance bar further includes a first end portion lengthwise outside of the first handle and having a second weight compartment associated therewith, and a second end portion lengthwise outside of the second handle and having a third weight compartment associated therewith. Each of the first and second foot platforms can have a push-up handle dock associated therewith. In some examples, the back-support portion of the base has a lumbar wheel removably mounted thereto.

In some embodiments, the system further comprises a plurality of IR lighting arms that project from the base. In some examples, each of the plurality of IR lighting arms can include a shape-memory adjustable shaft and a light strip disposed along a lengthwise portion of the respective IR lighting arm.

The headrest form can have raised, tapered lateral sides. In some implementations, the array of IR lights is arranged in a rectangular grid that covers a center portion of the back-support portion and extends from a front of the back-support portion, to and end of the back-support portion, and over the headrest.

In some implementations, the present disclosure relates to a multi-functional exercise system comprising a base including a body support portion positioned at a lateral center of the base and first and second foot portions positioned on opposite lateral sides of the body support portion. The system further comprises an array of infrared (IR) lights associated with an upper surface of the base.

In some examples, at least a portion of the body support portion is raised above the first and second foot portions. The array of IR lights can be integrated with a pad disposed on the body support portion of the base.

The system can further comprise a headrest removably couplable to a back portion of the body support portion, wherein a portion of the array of IR lights is disposed on an upper surface of the headrest. In some examples, the system further comprises a first resistance band tube coupled to a side of the first foot portion via a first pivot coupling, and a second resistance band tube coupled to a side of the second foot portion via a second pivot coupling.

The system can further comprise a resistance training bar coupled to at least one resistance band segment coupled to the base. For example, the resistance training bar can include first and second handles positioned on a front half of the resistance training bar, the first and second handles being angled relative to a central longitudinal axis of the resistance training bar, and first and second support bridges that pass behind the first and second handles, respectively.

For the purpose of summarizing the disclosure, certain aspects, advantages and novel features have been described. It is to be understood that not necessarily all such advantages may be achieved in accordance with any particular example. Thus, the disclosed examples may be carried out in a manner that achieves or optimizes one advantage or group of advantages as taught herein without necessarily achieving other advantages as may be taught or suggested herein.

BRIEF DESCRIPTION OF THE DRAWINGS

Various examples are depicted in the accompanying drawings for illustrative purposes and should in no way be interpreted as limiting the scope of the inventions. In addition, various features of different disclosed examples can be combined to form additional examples, which are part of this disclosure. Throughout the drawings, reference numbers may be reused to indicate correspondence between reference elements.

DETAILED DESCRIPTION

Figure 1A:
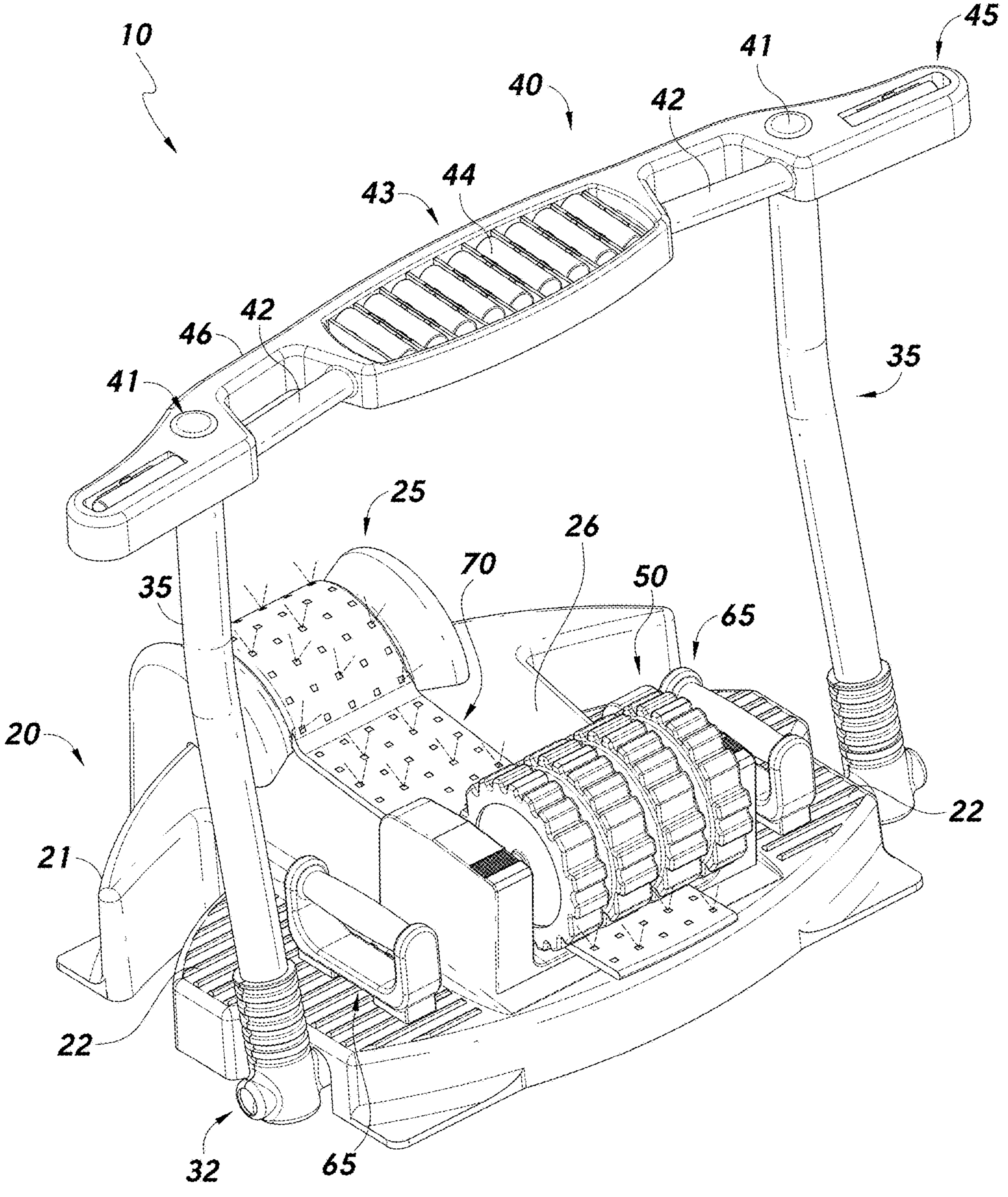
FIGS. 1A-1J show views of an infrared-integrated training system in accordance with one or more embodiments.
Figure 1B:
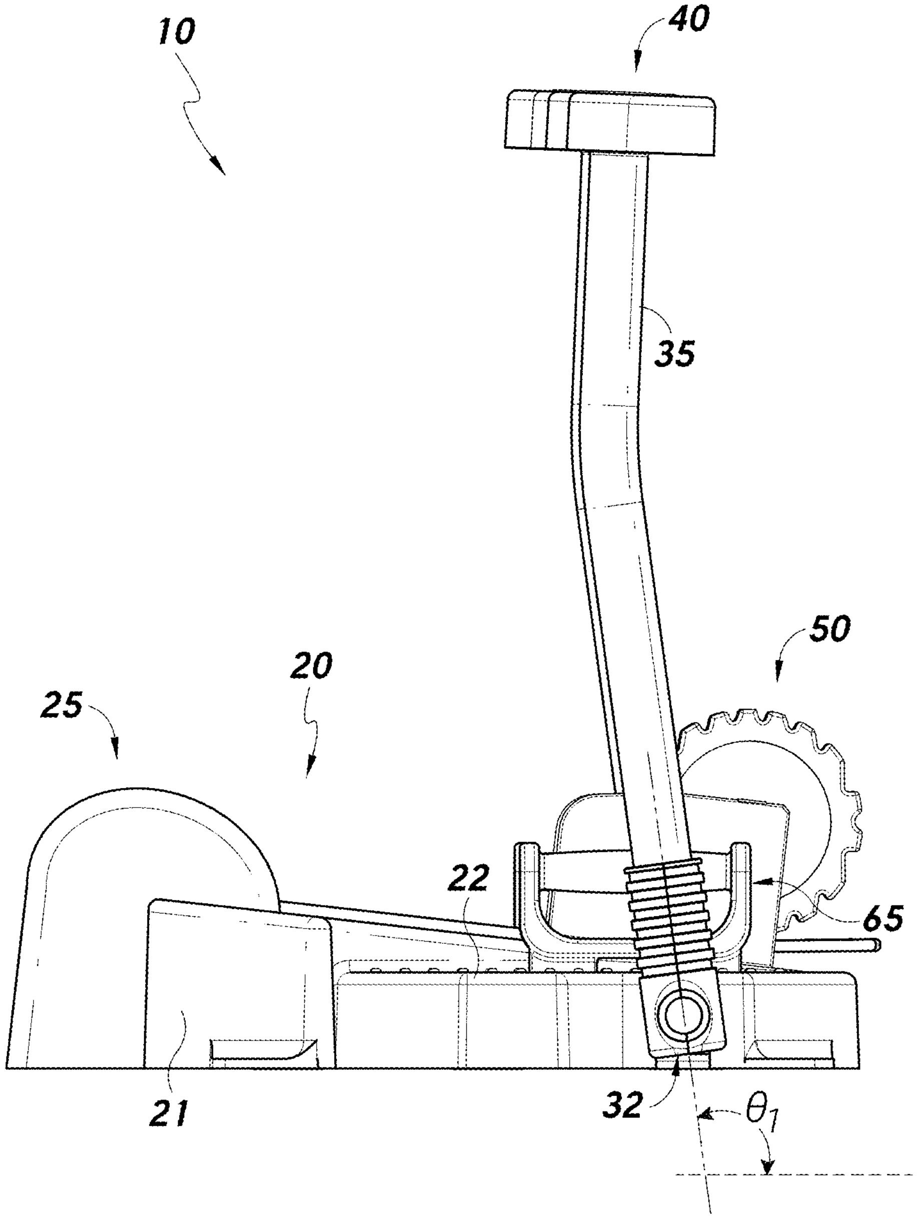
Figure 1C:
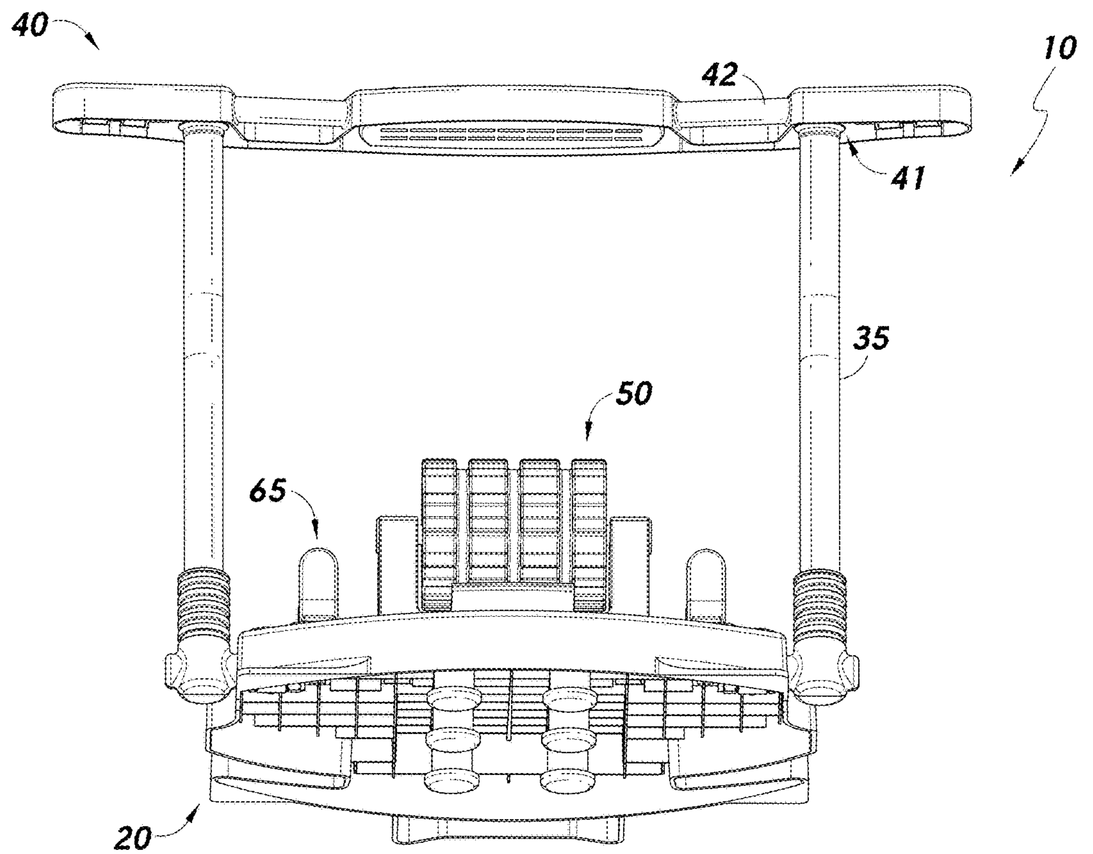
Figure 1D:
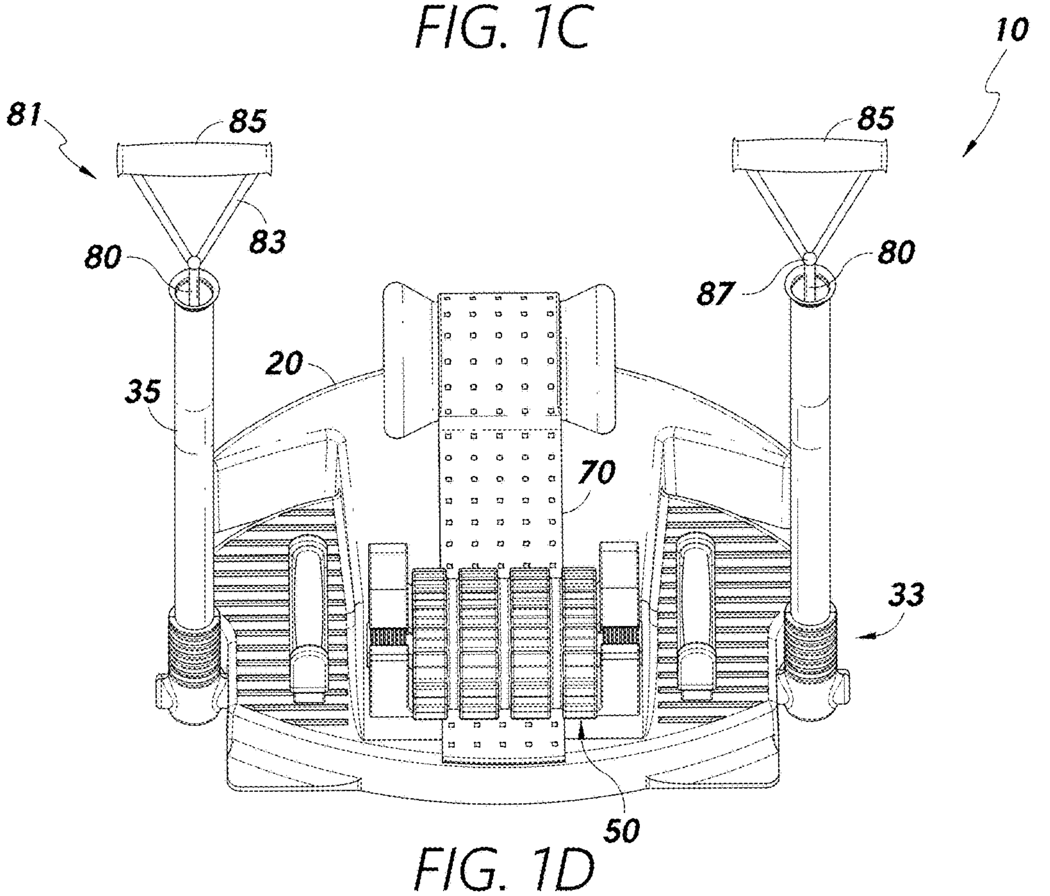
Figure 1E:
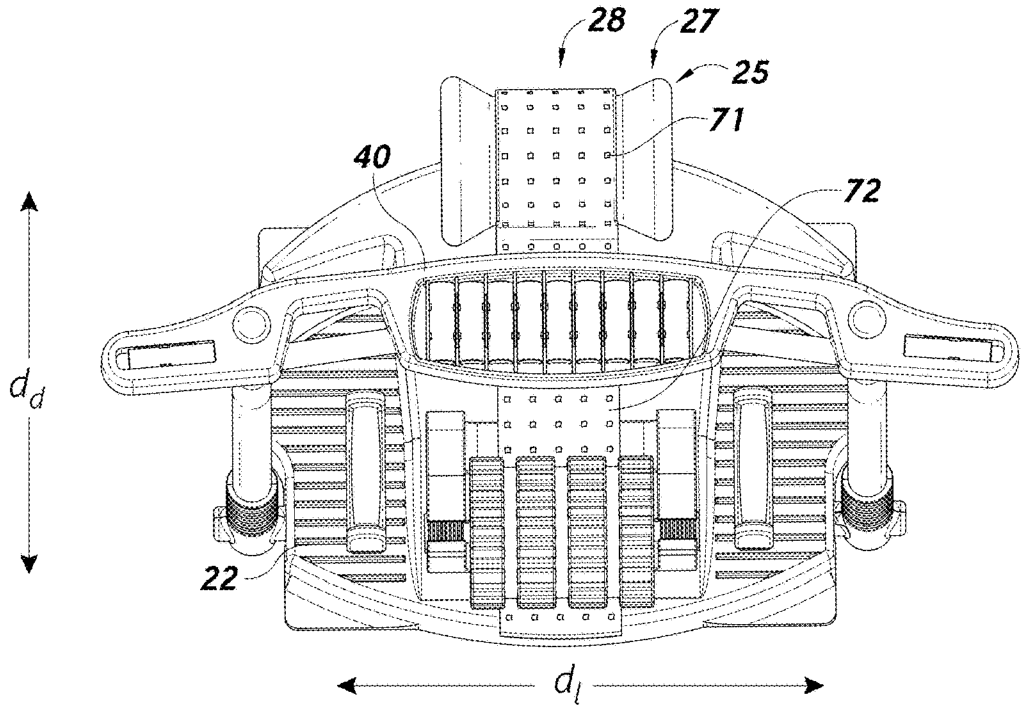
Figure 1F:
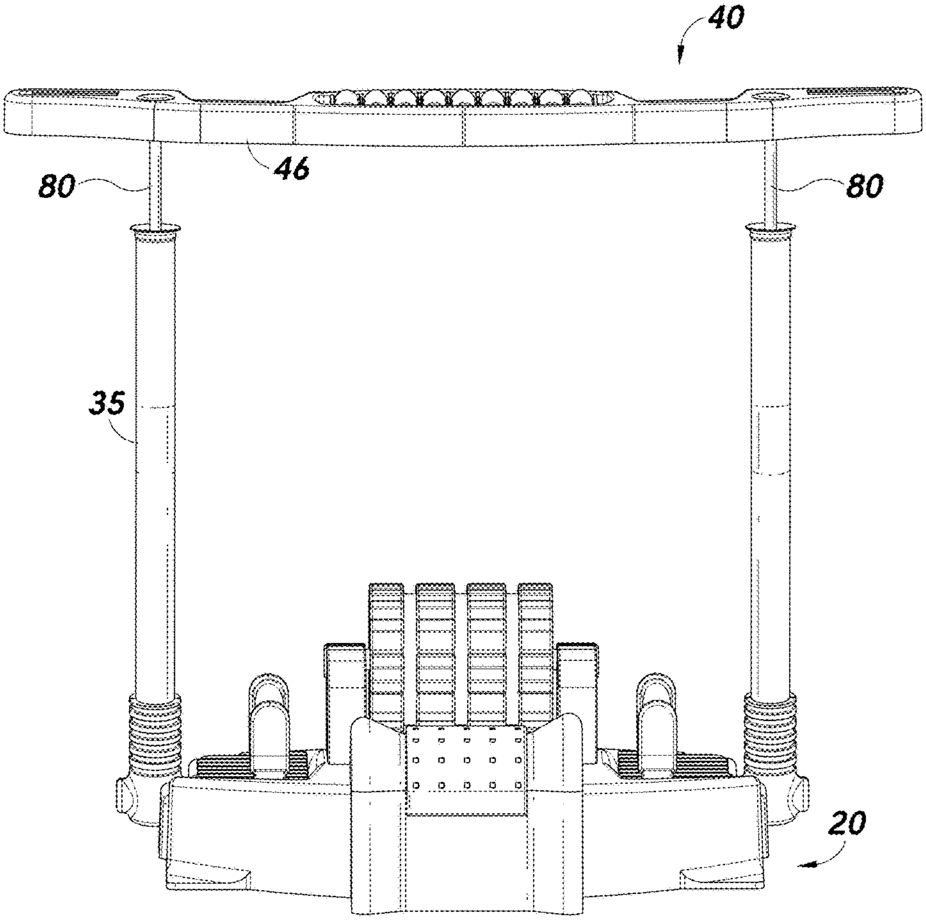
Figure 1G:
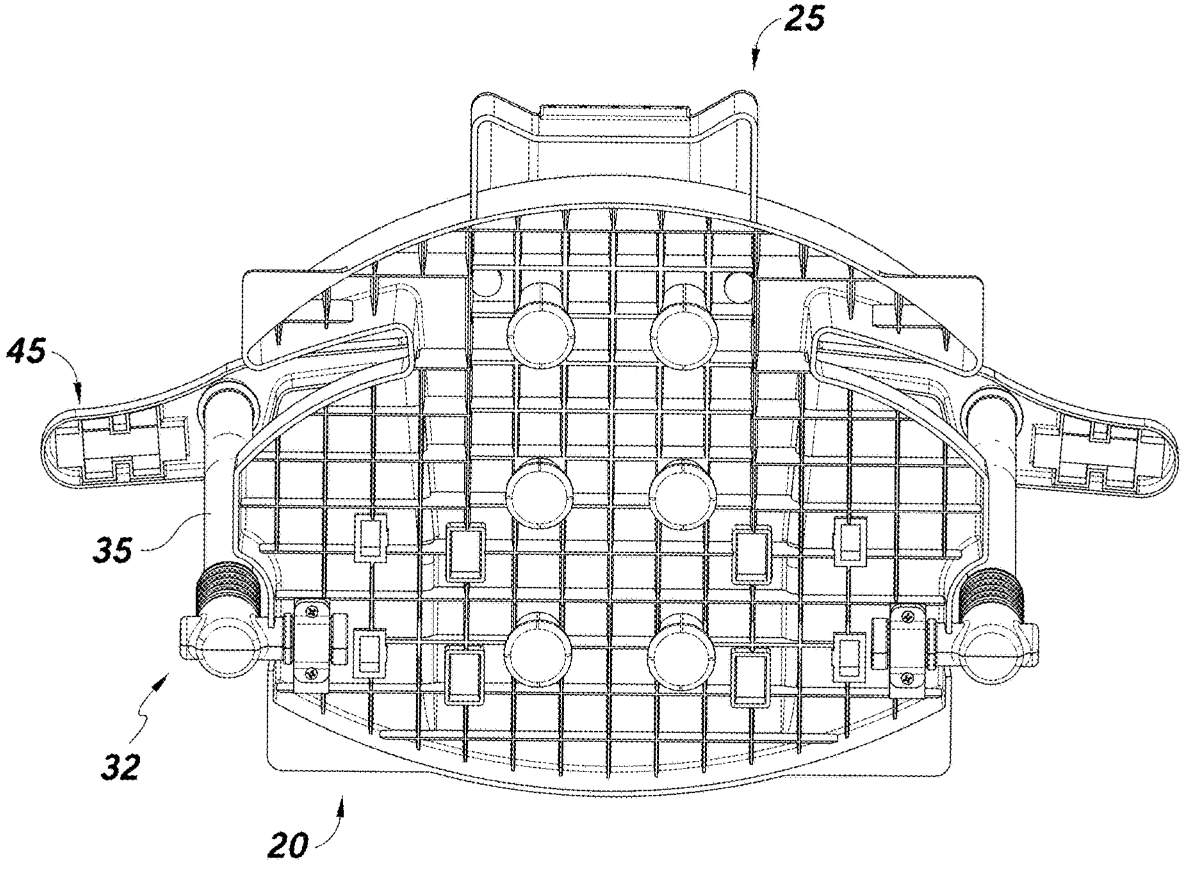
Figure 1H:
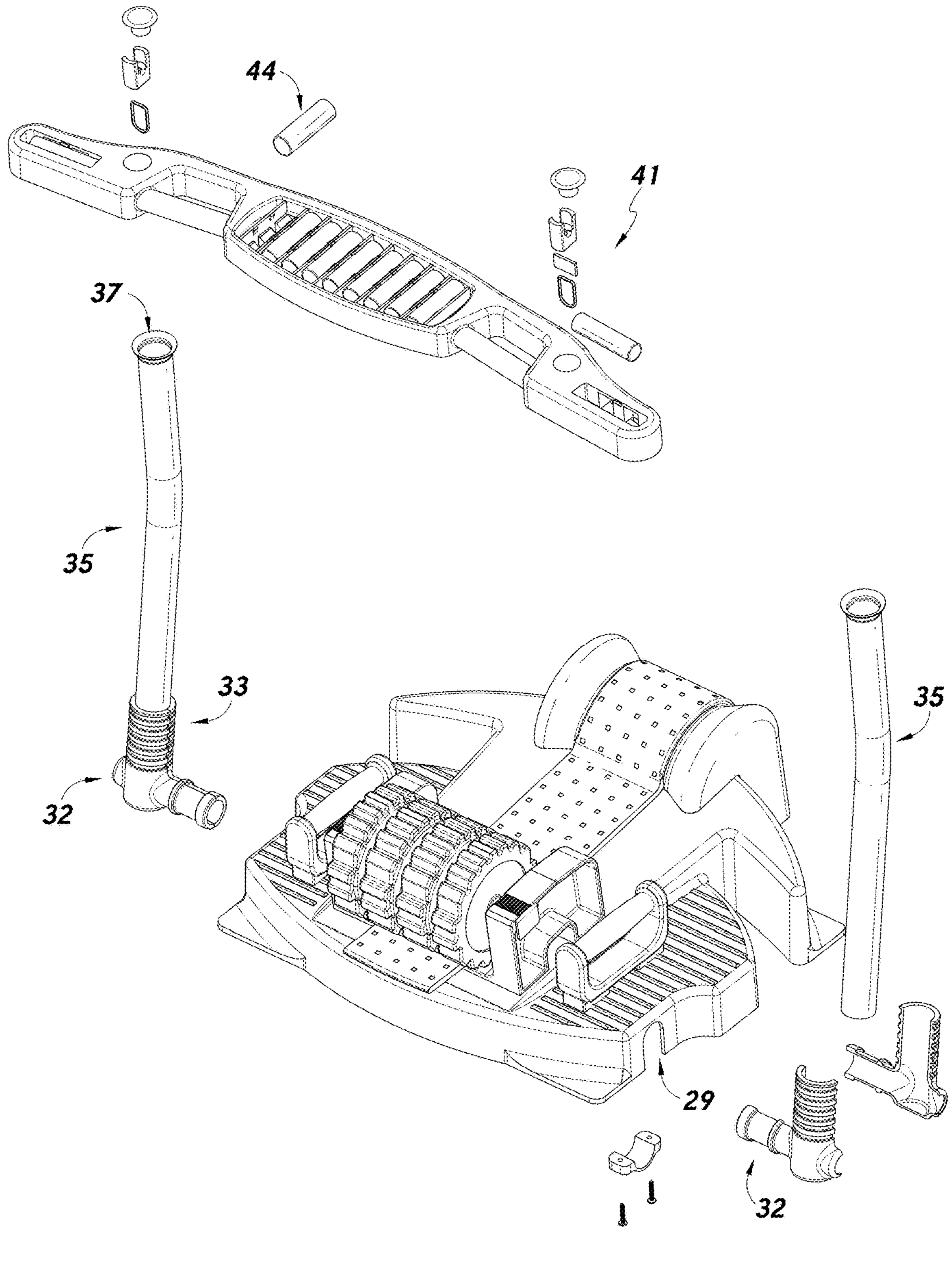

Although certain preferred examples are disclosed below, it should be understood that the inventive subject matter extends beyond the specifically disclosed examples to other alternative examples and/or uses and to modifications and equivalents thereof. Thus, the scope of the claims that may arise herefrom is not limited by any of the particular examples described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain examples; however, the order of description should not be construed to imply that these operations are order dependent. Additionally, the structures, systems, and/or devices described herein may be embodied as integrated components or as separate components. For purposes of comparing various examples, certain aspects and advantages of these examples are described. Not necessarily all such aspects or advantages are achieved by any particular example. Thus, various examples may be carried out in a manner that achieves or optimizes one advantage or group of advantages as taught herein without necessarily achieving other aspects or advantages as may also be taught or suggested herein.

Certain reference numbers are re-used across different figures of the figure set of the present disclosure as a matter of convenience for devices, components, systems, features, and/or modules having features that are similar in one or more respects. However, with respect to any of the examples disclosed herein, re-use of common reference numbers in the drawings does not necessarily indicate that such features, devices, components, or modules are identical or similar. Rather, one having ordinary skill in the art may be informed by context with respect to the degree to which usage of common reference numbers can imply similarity between referenced subject matter. Use of a particular reference number in the context of the description of a particular figure can be understood to relate to the identified device, component, aspect, feature, module, or system in that particular figure, and not necessarily to any devices, components, aspects, features, modules, or systems identified by the same reference number in another figure. Furthermore, aspects of separate figures identified with common reference numbers can be interpreted to share characteristics or to be entirely independent of one another.

Conventional resistance-training systems often lack integration with complementary therapy modalities, thereby missing opportunities to enhance the overall user experience and outcomes. In addition, many gyms have combined weight resistance or isoinertial and variable resistance bands tied to a weight bar, making them unbalanced and difficult to control. The use of red light (infrared, IR) therapy exercise in commercial and home gyms is currently limited to saunas and workout areas, with only standalone red-light units separate from fitness equipment. At present, there are no resistance training machines on the exercise market that combine red light therapy and resistance training in a single integrated unit designed for both home and commercial gym environments. Disclosed herein are infrared-integrated resistance systems/units that can provide more efficient and effective training solutions for users.

In some implementations, the present disclosure relates to exercise/training systems that include integrated infrared (IR) heat therapy pads/features for enhanced training and therapy. FIGS. 1A-1J show views of an IR lighting integrated, multi-functional, resistance and light therapy exercise/training system in accordance with certain embodiments of the present disclosure. The IR-integrated exercise system 10 includes a base 20, which can advantageously serve as a multi-functional support platform for the system 10. The base 20 can be designed to facilitate standing, seated, and/or lying exercises while integrating infrared (IR) therapy, resistance training, and/or push-up training functionality. The base structure 20 can incorporate various functional zones, including foot platforms 22, a back-support section 26, a headrest 25, and docking features for removable exercise/therapy components. Such portions/components may be considered part of a user-support top surface of the base 20.

The base 20 can have multiple sections, each designed to accommodate different workout positions and/or exercise modes. The base 20 may advantageously be constructed from a relatively durable, rigid material, such as reinforced polymer and/or metal (e.g., aluminum alloy, steel, composite hybrid), configured to provide sufficient stability to support typical human body weights under load on the user-support top surface of the base 20. The base 20 can include certain ergonomic contours and support zones, enabling comfortable positioning during different exercises. In some implementations, the base 20 includes rubberized or textured overlays in key contact area(s), such as in the foot platform areas 22, which can provide anti-slip properties. The base 20 can have reinforcing rib structures and/or hollow cavities to reduce weight while maintaining structural integrity. The various removable components of the base assembly 20 can be connected using integrated molding, screws, snap-fit features, and/or quick-locking joints, for example.

The base 20 can include two foot-standing platforms 22, which may be positioned on opposite (e.g., left and right) lateral sides, respectively, of the base 20 and/or back support section 26, allowing the user to stand securely while performing resistance-based exercises or other training. The foot platform(s) 22 can be flat, wide, and/or slightly textured structures to provide grip and stability for a user standing thereon. Each foot platform 22 may be structurally reinforced to support body weight during standing-based movements. The foot platforms 22 can be fixed to (e.g., integrated with) the base structure 20. The foot platforms 22 can include raised and/or recessed channels, grooves, and/or bars, which may run in a lateral dimension di, providing a gripping surface for added stability.

Push-up handle docking features 23 can be integrated into the foot platform(s) 22, allowing for removable push-up bar 65 installation. The docking features 23 can be configured as recessed mounting slots that allow for removable insertion/mating of attachment features 60 of push-up bars/handles 65 for secure push-up handle attachment. In some embodiments, the handles 65 can be removably inserted and locked in place using, for example, spring-loaded retention pins for a quick-lock mechanism, threaded insert fittings for a screw-in type connection, snap-fit connectors for tool-free removal, or similar mechanism. When the handles 65 are removed, the docking slots 23 may remain flush with the surface, allowing unobstructed standing use by the user. In some implementations, the push-up handles 65 and/or handle mount(s) 23 is/are configured to permit rotation and/or alternative positionings of the handles 65 for modifying push-up exercise angle.

The laterally-central portion of the base 20 includes an inclined back-support platform 26, designed to support the user's back (or chest) when lying or pressing against it. The back-support surface 26 may be slightly contoured, providing ergonomic lumbar support. In some embodiments, the base 20 includes foam padding over rigid support structure to provide a balance of comfort and stability. Such padding may be replaceable or removable for customization. The back-support surface 26 may be elevated, with respect to at least a portion thereof, above the food pads/platforms 22.

In some embodiments, a removable lumbar wheel 50 can be installed in a dedicated docking area 59 for rolling massage support during spinal stretching or resistance training. The rotating lumbar wheel 50 can be installed in dedicated docking channel(s)/receptacle(s) 59 associated with the back support. The wheel 50 can be removable, allowing users to customize their lumbar support during exercises. When installed, the wheel 50 can roll along the spine, providing massage-like spinal decompression and support during lying exercises (see FIG. 7). The docking feature(s) 59 promote alignment of the wheel 50 with the back support 26, preventing misalignment during use. The wheel may be positioned along the lower backrest area, where a user's lower back may be positioned when leaning against the base 20. In some implementations, the wheel is securable in a guide track for positional adjustment. In some implementations, the mounting feature(s) 59 provide docking recess(es) for snap-fit insertion. As shown in FIG. 1J, the lumbar wheel 50 may include a rotatable axle assembly/connection 55, allowing free-rolling movement of the user-contact wheel portion 52, which may comprise a high-density foam or rubber-coated wheel for comfort. The lumber wheel 50 may be used to enhance spinal decompression through massage-like rolling motion, and may be adaptable for various back-support training modes. A base 51 can be mounted to the system base 20, such as by inserting/mating mounting extensions 54 in corresponding mount recesses 59 in the base.

The base 20 further includes integrated infrared (IR) lighting feature(s) 70 for providing IR-enhanced training/therapy. For example, the integrated IR lighting feature(s) 70 may be implemented as an IR light pad/strip that runs across most of the back support width, providing light therapy to the user's back. The integrated IR lighting may be embedded within the back support panel 26, or may be a removable or otherwise configured IR lighting strip/pad. In some implementations, protective transparent or translucent covering may be disposed over the IR lighting to shield IR light elements from wear. The IR lighting 70 can advantageously be adjustable with respect to brightness and/or wavelength modulation for varied therapy applications, where such adjustment may be configurable through an input device associated with the base 20 and/or system 10, or through a connected software application. The IR lighting 70 may cover both back 26 and head/neck 28 portions of the base 20. For example, the IR lighting 70 may include an upper back segment 72, lower back segment 73, and a neck/head segment 71, as shown. In some implementations, the IR lighting is integrated with a pad that is disposed and/or attached on a user-support top surface (e.g., back-support surface/portion 26) of the base 20. Although shown as a rectangular strip/grid, it should be understood that the IR array/component can be arranged in any suitable manner in and/or on the base 20.

The base 20 can include a headrest 25 at a posterior aspect/portion of the base 20 adjacent the back-support portion 26. The headrest is positioned at the top/rear end of the back-support platform 26. The headrest 25 can be positioned just slightly rearward of the end of the foot pads 22, promoting proper alignment for head support when the user lies on the back support 26. The headrest 25 is positioned centrally in the lateral dimension $d_l$ between the foot pads 22, providing ergonomic alignment for neck and head support while allowing clearance for standing on the foot pads 22. The infrared (IR) light strip 70 may extend across the back support 26 in the depth dimension $d_d$ and continue onto the headrest 25, providing therapeutic coverage across the spine, neck, and head of the user. In some embodiments, the headrest 25 is padded for comfort and allows adjustable positioning to accommodate different user heights. The headrest can be removably couplable to the base 20.

Figure 1I:
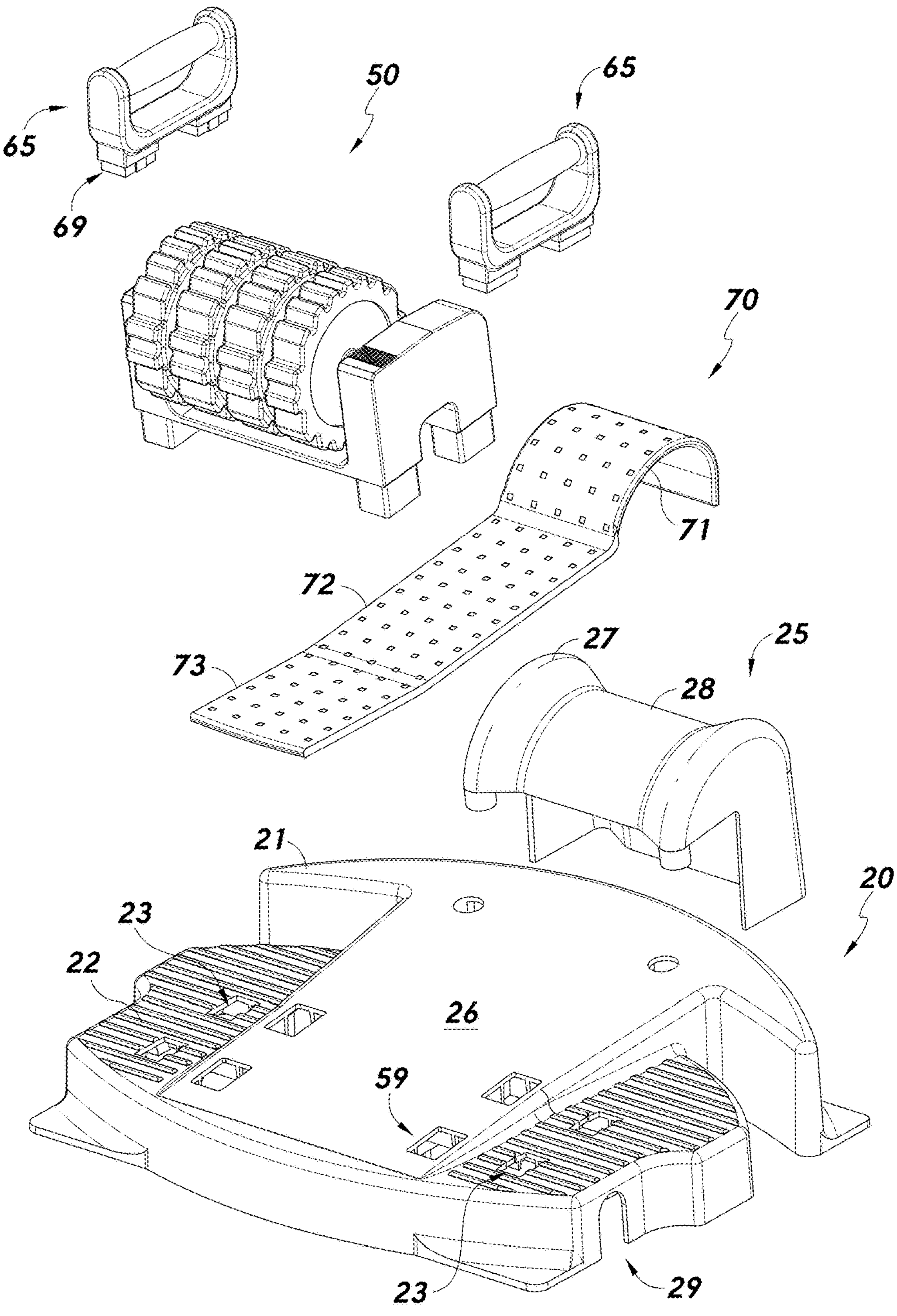
Figure 1J:
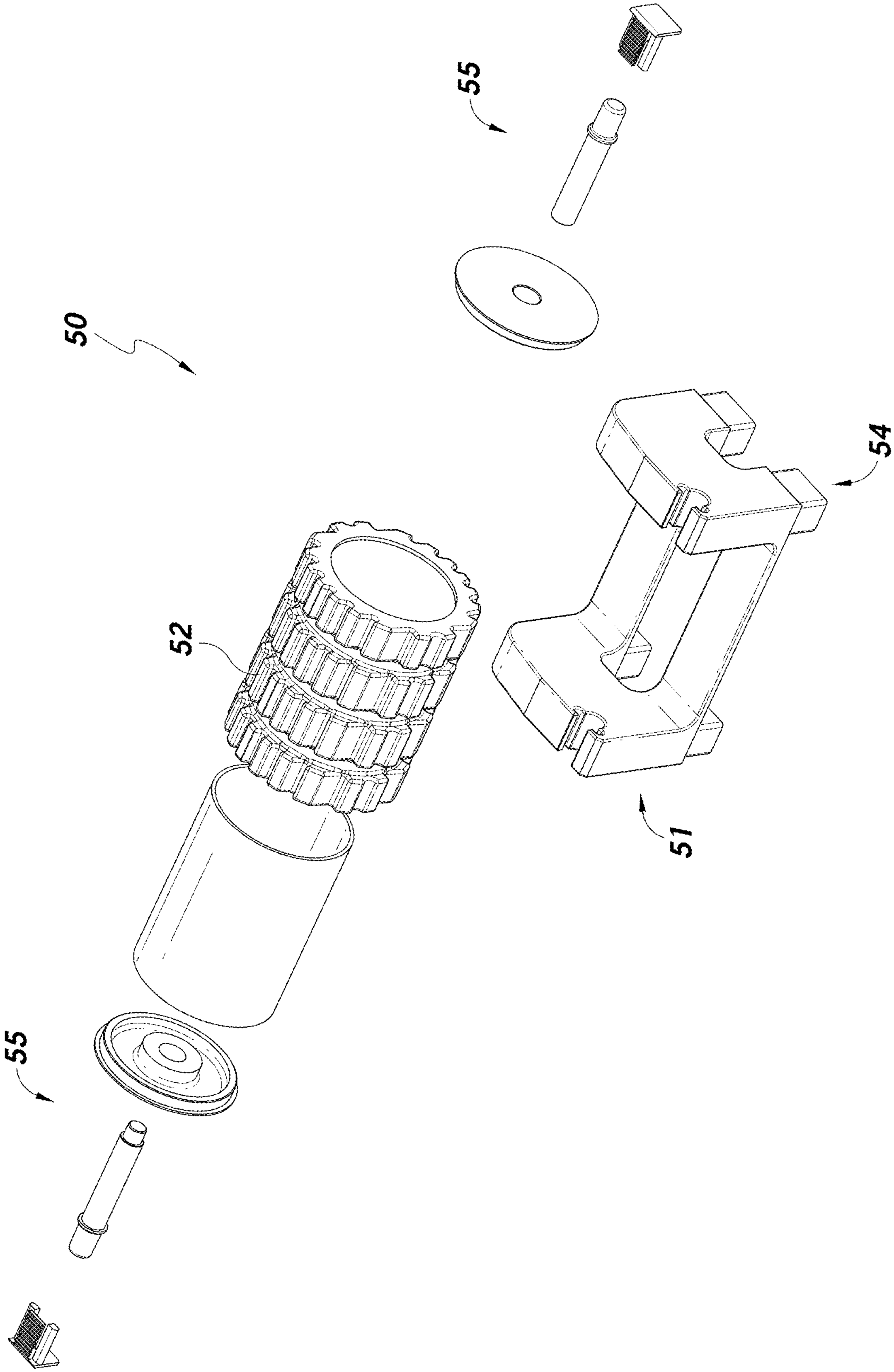

The headrest 25 may be removable from the base 20 in some implementations (see FIG. 1I). For example, mechanical coupling of the headrest 25 to the base 20 may comprise sliding track connection(s) that allow for positional adjustment and/or snap-in locking mechanism(s), which allow for quick removal. In some implementations, Velcro, magnetic, or soft retention mechanism(s) may be utilized for ease of configuration. The headrest 25 may include memory foam or gel cushioning to enhance comfort and/or breathable, washable covering for hygiene and durability. In such embodiments, the IR lighting 70 may advantageously be integrated with the cushioning/covering. In some embodiments, the central portion 28 of the headrest 25 is relatively flat or gently contoured to cradle the back of the user's head, whereas the lateral sides 27 of the headrest 25 are raised, tapering upward and outward from the central portion 28. This tapered design can advantageously restrict lateral head movement, which may be useful when the user is engaging in resistance exercises (e.g., pressing movements) and/or stretching or recovery positions. In some implementations, the IR light strip 70 does not cover the raised side portions 27, or alternatively, the side supports 27 may also have integrated IR lighting. The raised side sections 27 may have gradual or stepped elevation, depending on the design. The tapered upward contouring of the side portions 27 can beneficially restrict excessive side-to-side head movement, reducing strain on the neck and cervical spine, while maintaining the user's head in an optimal position when lying on the IR light strip 71 for infrared therapy. The gradual taper provides an adaptive fit that accommodates users of various head sizes without being unduly restrictive.

The base 20 may comprise wing-like shoulder supports 21 extending laterally outward from the center of the base 20, which may provide structural support/balance for the base and/or upper-body support for a user's shoulders/arms when lying on the base 20. The shoulder-supports 21 may extend outward from the neck/head support area, providing stabilization during pressing and lying exercises. The shoulder support 21 can have cushioned padding overlays for additional support and comfort.

In the illustrated example, a rectangular infrared (IR) light strip 70 runs along a depth dimension $d_d$ of the base 20 and/or back-support platform/surface 26, further extending along the headrest 25. The IR light array 70 can comprise or consist of, for example, one, two, three, four, five, six, seven, eight, or more rows/columns of IR light sources distributed in the lateral dimension $d_l$ (five rows shown), forming a grid pattern with a desirable number of rows/columns distributed in the depth dimension $d_d$. The light strip/grid 70 can advantageously provide IR therapy to the user's back, shoulders, head, and/or other body parts when the user is positioned on the base 20 and/or performing exercises such as push-ups (see FIG. 3; chest and facial IR exposure), lying exercises (see FIG. 8; spinal and muscular IR exposure), seated or pressing exercises, or other system usage. In terms of IR wavelength and power, the IR lighting strip/grid 70 can be configured to emit near-infrared (NIR) spectrum (~850 nm to 940 nm) light for deep tissue penetration. In some embodiments, the IR lighting 70 is adjustable with respect to intensity settings to regulate heat output and/or therapeutic effectiveness. For example, the system 10 may include integration of touch-sensitive and/or wireless control mechanism(s) for adjusting IR wavelength and/or power. The system 10 can include a battery power source and/or wired power supply.

The system 10 includes rotationally positionable resistance band members/tubes 35 configured to be secured to the base 20 and house resistance bands/elements 80, which may be entire independent bands, or segments of one or more bands (e.g., band segments). The resistance band support tubes 35 serve as structural mounting elements for the enclosed resistance bands 80, enabling controlled elastic force application during various resistance training exercises. The support tubes 35 can advantageously be rotationally adjustable between a flat (see FIG. 3) or articulated (see FIG. 1A) orientation, allowing for user-customizable resistance training angles and/or storage configuration. The tubes 35 can be used with interchangeable resistance handles 85 (see FIG. 1D) or an alternative resistance bar assembly 40.

Figure 3:
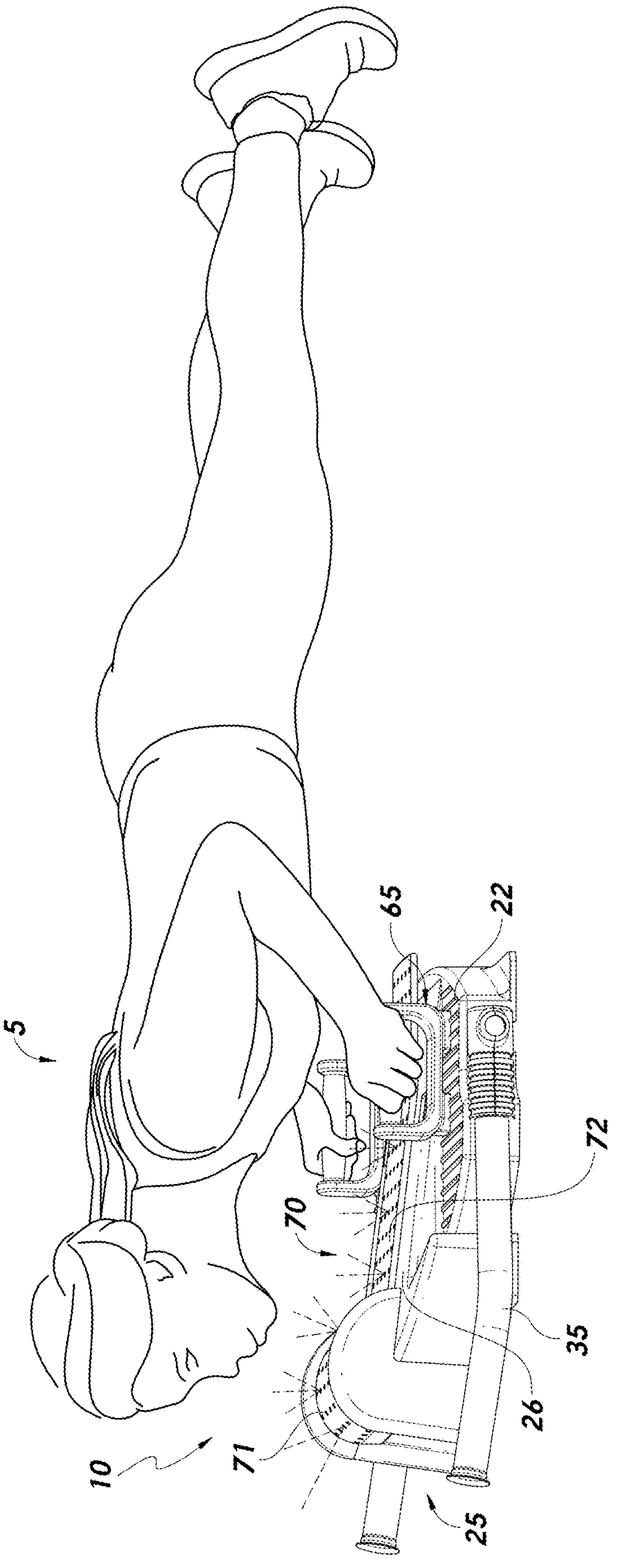
FIG. 3 shows a user engaged in a push-up exercise while utilizing a multi-functional, infrared (IR) integrated training system in accordance with one or more embodiments.

The resistance band support members/tubes 35 can comprise elongate, hollow structures mounted on the anterior aspect of the base 20, positioned adjacent to the foot platforms 22. The tubes 35 serve as enclosures/housings for the resistance bands 80, allowing for guided band movement during force application. In some embodiments, the resistance band supports 35 can be implemented as non-tube structures, such as extension rods with distal resistance band rings/guides, or as extension rods/members with distal resistance band attachment features (e.g., the resistance bands may not extend a length of the extension rod/member). The tubes 35 can be constructed from rigid, lightweight materials, such as reinforced polymer composites, aluminum alloys, or carbon fiber to provide high tensile strength, impact resistance, and/or minimal flex under loading conditions. The resistance band support tubes 35 can be pivotally coupled to the base 20 via rotational joints 32, permitting controlled articulation between multiple positional configurations. For example, the tubes/bars 35 may be positionable in a flat position in horizontal alignment with the base 20, as shown in FIG. 3 and other figures. The joint 32 may couple to a cutout/slot 29 in the side of the foot platforms 22. To position the tubes 35 in the flat configuration (e.g., storage configuration), the tubes 35 may be rotated downward, resting in substantially parallel alignment with the bottom surface of the base 20. Such configuration can be suitable/optimized for low-profile storage, ground-based resistance exercises, or for positioning the tubes 35 out of the way for certain training/therapy not involving use of the resistance bands 80, such that the tubes 35 to not interfere with user body placement or movements. The tubes can have accordion portions 33, as shown, for providing axial/lengthwise flexibility for compression and/or expansion.

Alternatively, in an articulated position (e.g., angled or vertical configuration), the bars/tubes/shafts/members 35 can be rotated upward, positioning the exit points of the resistance bands 80 at an elevated height above the base 20. Such configuration can advantageously allow placement of the tubes 35 at a desired angle $\theta_1$ for full-range resistance movements, accommodating vertical, diagonal, and lateral resistance vector applications. In some exercises, it may be desirable to rotate the tubes to a position substantially perpendicular to the bottom surface of the base 20 (e.g., the plane of the ground surface). In the stowed configuration, the tubes/members 35 may be rotated to an angle substantially parallel with the bottom surface of the base 20. As used herein, description of an angle being "substantially" parallel or perpendicular to a plane means within 10° of parallel or perpendicular, respectively. The rotational positioning mechanism may incorporate one or more of the following locking and articulation features: indexed detent positions or preset angular stops to maintain stable positional settings, friction-based rotational damping mechanisms to prevent unintended movement, spring-loaded or cam-lock engagement members for secure angular adjustments, and/or quick-release locking pins enabling user-controlled repositioning.

Each resistance band 80 is routed internally through its respective support tube 35, wherein the resistance bands 80 may be fixed to a bottom of the base 20. In some implementations, the resistance bands 80 are separate segments of a single band that runs through or under the base 20 and through both support tubes 35. In some examples, each resistance band 80 is anchored at a proximal end to the base assembly 20, with a distal end/portion extending outward through a distal exit aperture/opening 37 at the upper portion of the respective tube 35. The exit aperture 37 geometry may include low-friction grommets or bushings to minimize band wea, reinforced guides or pulleys to facilitate smooth band movement, and/or self-aligning band tracking mechanisms to accommodate multi-directional resistance applications.

The distal ends of the resistance bands 80 may include connectors or features for interchangeability of resistance handles and resistance bar connections. For example, the distal end of each resistance band 80 may feature a quick-connect attachment mechanism, enabling secure and rapid interchangeability between resistance handle component 81 attachment and resistance bar 40 attachment. The resistance handles 81 may have a triangular frame band/structure coupled to a grip bar 85 (e.g., foam-covered and/or ergonomically-contoured). The grip bar 85 may be coupled to cord or webbing strap extensions 83 that converge at an attachment point 87, forming the triangular profile. The attachment mechanism 87 can promote swivel-free yet flexible connection, allowing free wrist articulation during pulling and pressing movements.

The system 10 can include a resistance bar 40, which comprises a rigid, elongate structural member designed for bilateral resistance-based strength training. The resistance bar 40 is mechanically configured to interface with the resistance bands 80 housed within the rotationally-positionable support tubes 35, allowing for adjustable force application through controlled elastic resistance, though the resistance bar 40 may be detachable for the bands 80 and/or usable separately from the bands 80 and/or system 10. The bar 40 can feature ergonomic handle positioning, modular weight attachment functionality, and/or a quick-connect system for interchangeability with resistance handles.

The resistance bar 40, shown in various views in FIGS. 13A-13J for additional reference and clarity, comprises a central elongate body extending in a lengthwise dimension 1, which may be fabricated from a lightweight, high-strength material, such as aluminum alloy, carbon fiber composite, reinforced polymer, or similar construction. The bar 40 features a primary gripping zone positioned forward of the central longitudinal axis l, which positioning can advantageously promote proper biomechanical engagement during use. The forward-biased position of the handles 42 can enhance wrist positioning, reduce joint strain, and/or improve force alignment during pressing and pulling movements. The handles 42 can have contoured shaping to accommodate a natural hand posture. For example, the handles may be slightly angled by an angle $\theta_2$ that is between 1-20°, such as between 1-5°. The handles 42 can include non-slip, high-friction surface treatment (such as textured rubber or foam padding) and/or vibration-dampening properties to improve user comfort during high-tension exercises. The handles 42 may be integrally formed with the bar body or modularly attached for adjustability. Support bridges/bars 46 may pass behind the handles 42 to provide additional support to for the bar 40. The handles may be positioned on a front half of the bar 40 (i.e., in front of the central longitudinal axis l of the bar, as shown; see FIG. 13E).

The resistance bar 40 can incorporate a centrally positioned weight attachment system/compartment 43, allowing for variable resistance augmentation. For example, cylindrical or rectangular weights can be mounted in the central portion/compartment 43 of the bar 40, which may be positioned transversely relative to the bar's longitudinal axis l, as shown, or otherwise oriented. The weights 44 can be utilized to increase the effective resistance load of the bar 40, which may be in addition to the force applied by the resistance bands 80. The weight compartments can advantageously be balanced along the length of the bar 40 to provide stability while preventing unbalanced torque forces. The weights 44 can be secured to the bar using a modular locking system, which may include threaded engagement (twist-lock mechanism), quick-release pin locking for tool-free weight adjustments, magnetically secured inserts to facilitate rapid weight changes, and/or other attachment mechanism(s). The central weight attachment segment/compartment 43 may be positioned between the handles 42, as shown. The weight system allows users to increase or decrease resistance by attaching or removing weights, enabling progressive overload training.

The portions 45 of the bar 40 extending longitudinally/lengthwise outside of the handle grips 42 defines the overall length of the bar 40. The end segments 45 serve as a structural extension for resistance band connection points 41, allowing for smooth force distribution. The end segments 45 can further act as an interface for resting the bar 40 on the support structures 35 when not in use. These sections may be cylindrical, flattened, or reinforced with ribs to increase stiffness without excessive weight addition. The distal ends 45 of the bar 40 can include rounded projections that extend beyond the resistance band connection points 41.

Just outside the handles 42, the resistance bands 80 can be anchored to the bar 40 via swivel-mounted connectors (allowing flexible band movement), carabiner or clip-style locking mechanisms (for quick attachment/detachment), and/or integrated strap loops or reinforced eyelets (for durable band anchoring). The connection points 41 can be positioned as shown to prevent interference with the user's grip, uneven tension distribution during dynamic exercises, and unnecessary torque on the bar structure. The outermost bar sections/segments 45 may also incorporate removable weights/inserts for further fine-tuning of the resistance profile.

With further reference to the resistance bar 40, the weights may be elongate in shape, as shown, and may be oriented perpendicular or parallel with the central longitudinal axis l. The handles 42 may be symmetrically-angled relative to the axis l. For example, the handles 42 may be angled at a similar angle, but in opposite directions, as shown. The handles 42 may laterally span a pocket/void/cut-out in the elongate body of the resistance bar 40, as shown. The pocket/void/cut-out may be forward-facing and defined by lateral angled walls that lead into the posterior support bridges 46. That is, the lateral sidewalls that define the pocket/void/cut-out spanned by the handle 42 may lie in planes that converge in space behind the resistance bar 40.

The elongate body of the resistance bar 40 may be at least partially curved, such that the rounded/curvilinear (e.g., dome-shaped) end portions/termini 45 are positioned forward/in-front of the central axis l. The rounded end portions 45 may have a transverse/minor-axis dimension that is narrowed/lesser compared to the transverse/minor-axis dimension of the central weight-attachment section/portion 43 (i.e., the dimension of the central portion 43 perpendicular to the axis l).

Figure 2:
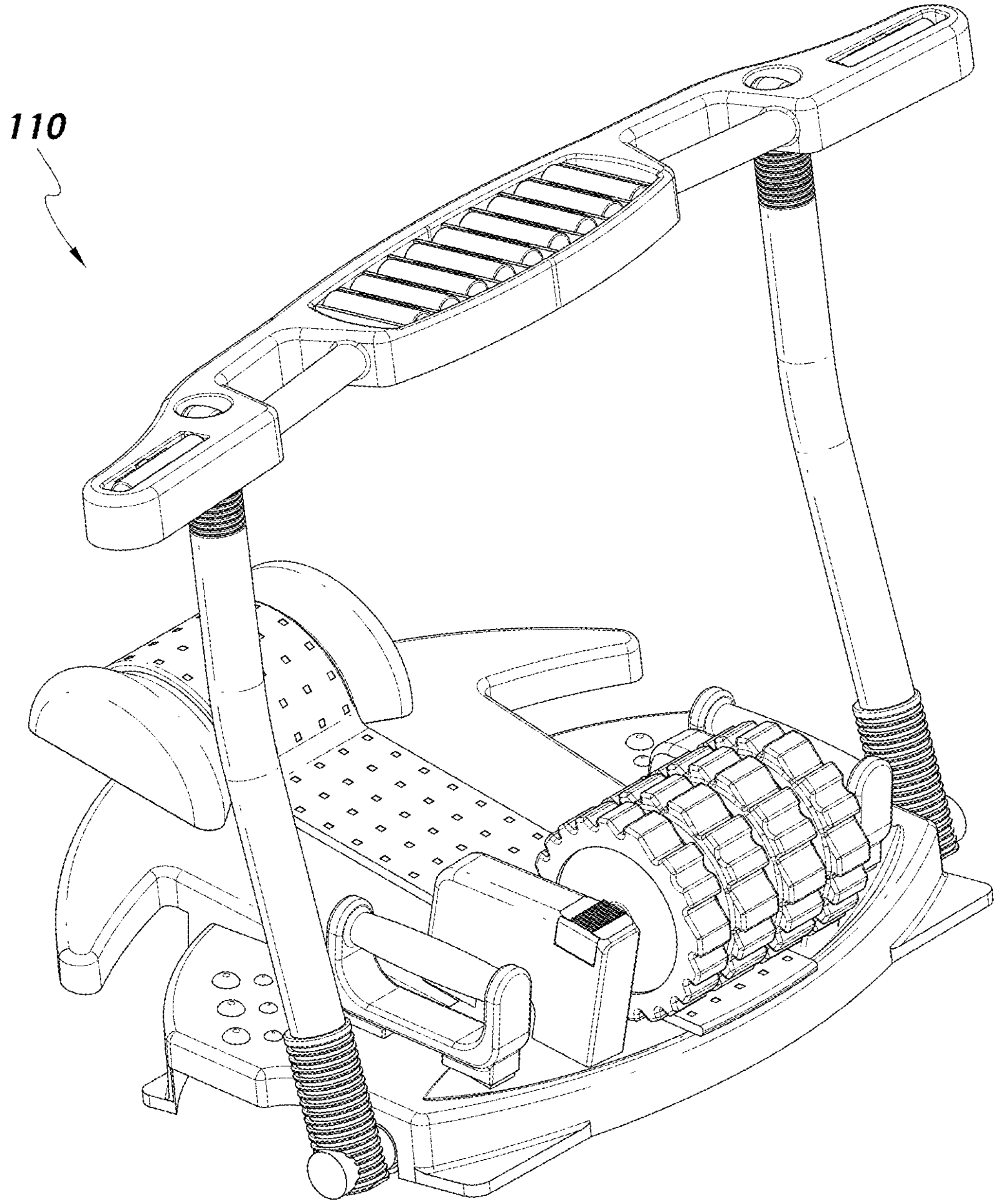
FIG. 2 shows a perspective view of an infrared-integrated training system in accordance with one or more embodiments.

FIG. 2 shows a perspective view of an infrared (IR) lighting integrated resistance training system 110, which may include any of the features described above in connection with FIGS. 1A-1J. As shown, various components of the system 110 may be somewhat modified structural design, dimensions, and/or configurations compared to corresponding components of the system 10 shown in FIGS. 1A-1J and described above.

FIGS. 3-13, which depict training and therapy systems that may have any of the features of the system 10 described in FIGS. 1A-1J, can be understood with reference to the depictions and description of FIGS. 1A-1J. FIG. 3 shows a user 5 engaged in a push-up exercise while utilizing a multi-functional, infrared (IR) integrated training system 10 as described herein in accordance with one or more embodiments. The system 10 is configured to provide resistance-based training, IR light therapy, and ergonomic support, promoting effective and safe exercise. The user 5 is positioned in a standard push-up stance, with hands gripping the push-up handles 65 that are mounted to the foot platforms 22 on either side of the back-support surface 26. The user's body is aligned along the depth dimension $d_d$ of the training system 10, with feet extending rearward and torso positioned at least partially above the back-support surface 26. The IR-integrated system 10 advantageously provides a resistance-based exercise system that allows simultaneous muscle engagement and passive recovery benefits.

The arms of the user 5 extend downward from the shoulders, with the wrists in a neutral position due to the ergonomic orientation of the push-up handles 65. The push-up handles 65 are secured to the foot platforms 22, providing a stable gripping surface while enabling a full range of motion during the push-up movement. The integrated IR light strip 70 emits IR light directed upward toward the user 5. The IR illumination may be generally directed to the anterior portion of the user's body. For example, the IR light may advantageously shine on the chest, providing targeted light therapy to the pectoralis muscles and surrounding tissues. The IR light may further shine on the user's arms, particularly the forearms and biceps, aiding in circulation and recovery enhancement. The user's neck may further benefit from IR light exposure in the form of increased localized blood flow and potential muscular relaxation. The portion 71 of the IR light strip 70 that is associated with the headrest 25 can advantageously emits IR light upward toward the user's face and neck, which can improve circulation and potential recovery effects.

In the configuration shown in FIG. 3, the resistance band support tubes 35 are shown in a stowed position, oriented substantially parallel with the ground. In this retracted or stowed configuration, the resistance band support tubes 35 remain out of the way of the user's arms and shoulders, allowing for unobstructed execution of the push-up movement. Such configuration can be enabled by rotatable mounting of the tubes 35 to the base 20, which allows the user to pivot the tubes 35 downward to prevent interference with upper-body movements.

Figure 4A:
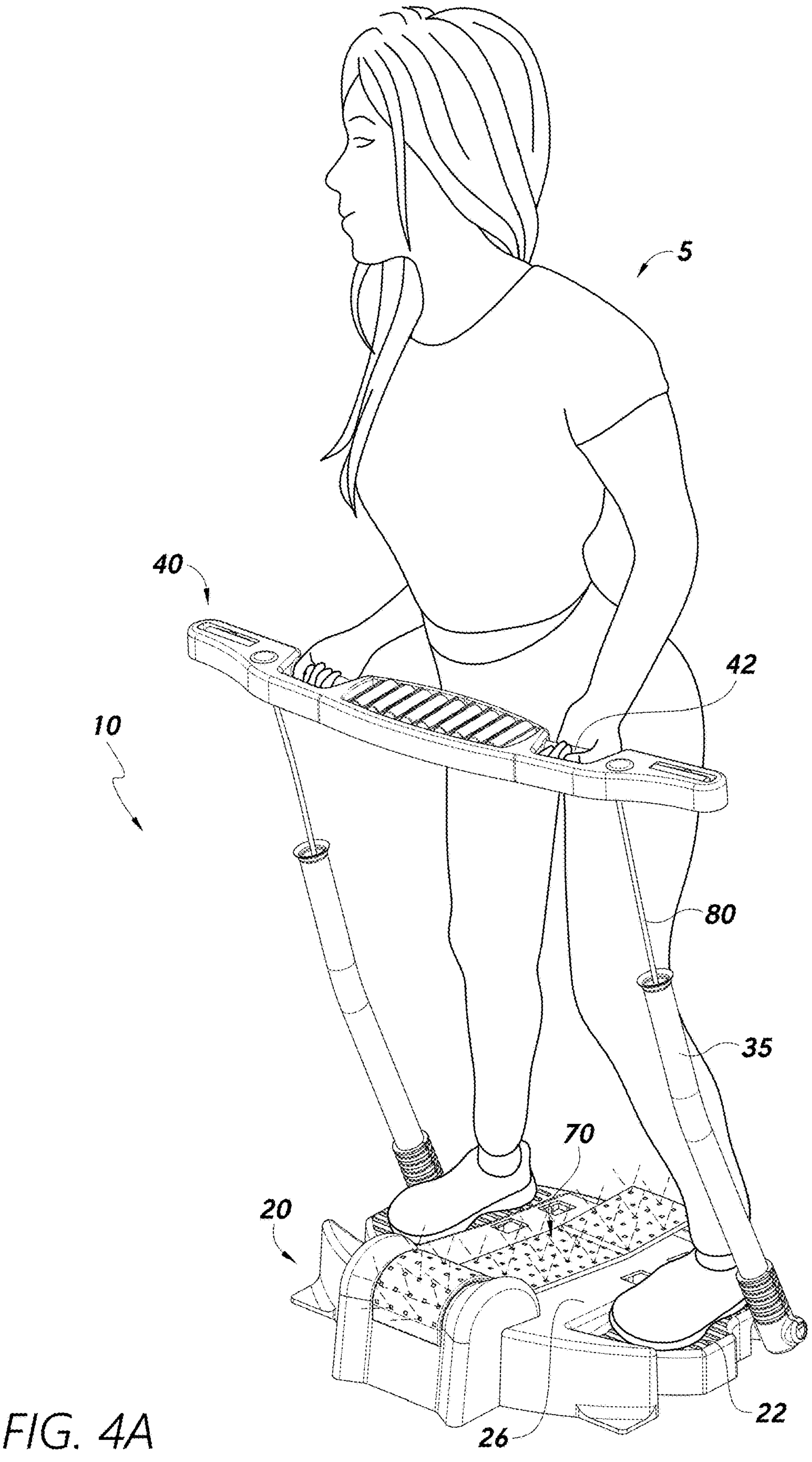
FIG. 4A shows a user engaged in a curl-type resistance exercise while utilizing a multi-functional training system in accordance with one or more embodiments.

FIG. 4A shows a user 5 engaged in a curl-type resistance exercise while utilizing the multi-functional training system 10. With respect to curl exercises, the system 10 advantageously provides adjustable resistance training, infrared (IR) light therapy, and ergonomic foot placement, promoting optimal user engagement and biomechanical alignment.

The user 5 is shown standing upright on the foot platforms 22, positioned with feet shoulder-width apart for a stable stance during the resistance training movement. The foot platforms 22 are laterally spaced on either side of the back-support surface 26, promoting a balanced user position for standing-based exercises. The user is shown gripping the handles 42 of the resistance bar 40 in a supinated (palms-up) grip, with hands positioned in front of the torso, allowing for controlled execution of a curl-type resistance movement. The resistance bar 40 is mechanically coupled to the resistance bands 80, which extend downward through distal openings of the resistance band support tubes 35. The user's arms are flexing at the elbows, lifting the resistance bar 40 upward toward the chest, activating the biceps, forearms, and stabilizing muscles.

The back-support surface 26 includes the integrated infrared (IR) light strip 70, which emits IR light directed upward toward the user's lower body. The IR illumination may provide light therapy exposure to the legs, including the quadriceps and calves, supporting muscle relaxation and circulation enhancement during the exercise. The lower torso, including the hip flexors and abdominal region, may further be exposed to the IR light, promoting broad coverage of muscle groups engaged in postural stabilization.

The resistance band support tubes 35 are positioned in an active, upright orientation, allowing for optimal resistance force application. The resistance bands 80 extend from the distal openings of the support tubes, creating a direct resistance force vector aligned with the upward movement of the resistance bar 40.

The resistance bands 80 are tensioned as the user lifts the resistance bar 40, generating a progressive resistance profile that increases as the bands stretch. The pivotally mounted resistance band support tubes 35 ensure proper band guidance, preventing excessive lateral band movement or misalignment. The user grips the resistance bar 40 at the handles 42, which are biased forward relative to the bar's primary longitudinal axis. The resistance bar 40 may be structurally reinforced to enhance stability under tension loads, such as may be experienced when performing curl exercises. The mechanical connection between the resistance bands 80 and the resistance bar 40 may include any suitable or desirable mechanism(s), such as swivel-mounted connectors, quick-connect locking mechanism(s) (e.g., for seamless interchangeability with alternative resistance handles), and/or high-tensile, reinforced attachment points to reduce premature wear of band connection interfaces.

Figure 4B:
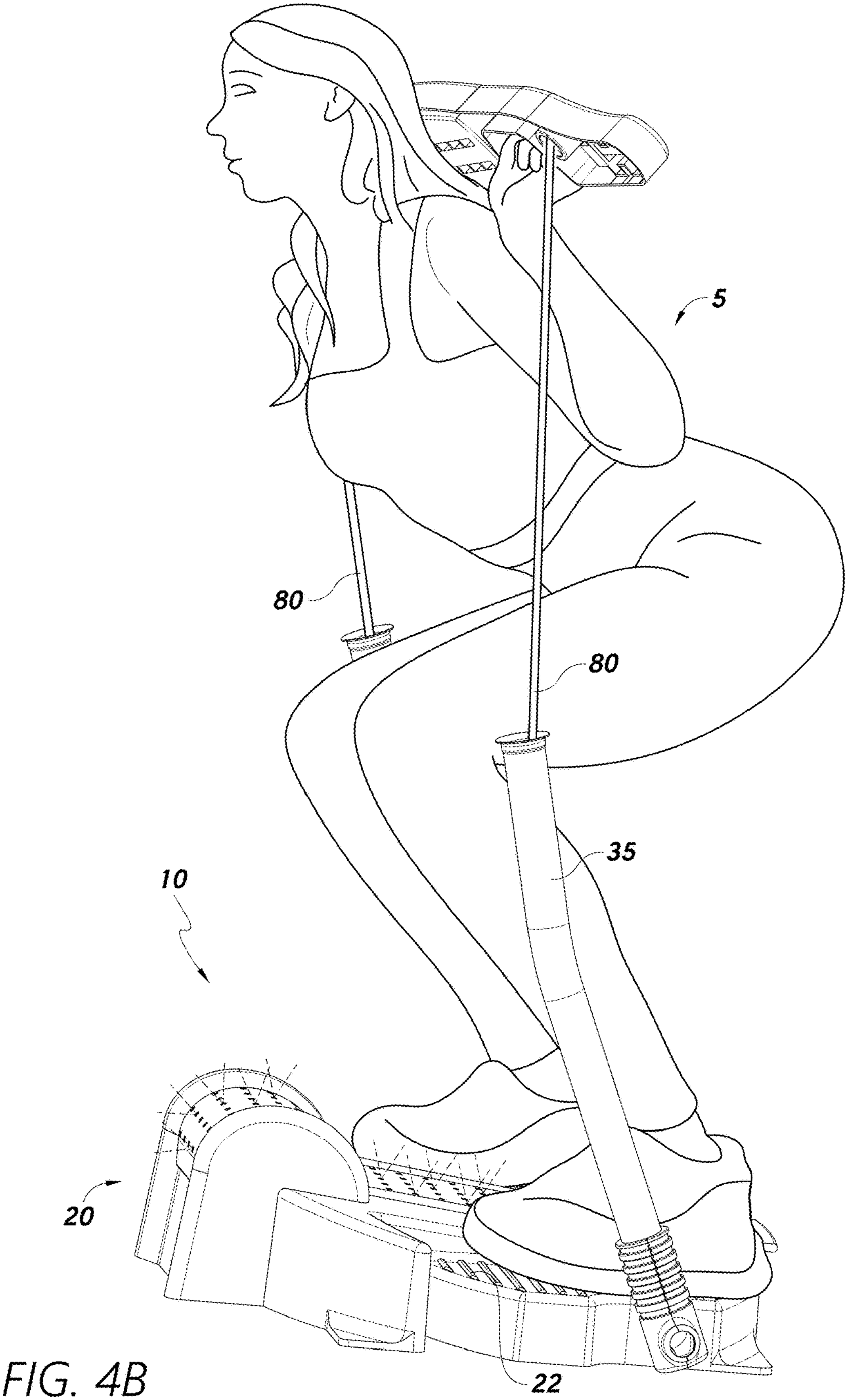
FIG. 4B shows a user engaged in a squat-type resistance exercise while utilizing a multi-functional, infrared-integrated training system in accordance with one or more embodiments.

FIG. 4B shows a user 5 engaged in a squat-type resistance exercise while utilizing the multi-functional, infrared-integrated training system 10. The user 5 is shown standing on the foot platforms 22 with a shoulder-width stance, promoting stability during the squat movement. The resistance bar 40 is positioned across the user's upper back, resting against the posterior neck and shoulders. The user's hands grip the handles 42 of the resistance bar 40, securing the bar in position while allowing for controlled force application. The user is shown in a position actively squatting, with the knees bending and hips lowering while maintaining an upright torso posture.

The resistance bands 80 are tensioned as they extend from the distal openings of the resistance band support tubes 35, providing regressive/progressive resistance force as the user lowers into the squat and rises back to a standing position. The back-support surface 26 includes the integrated infrared (IR) light strip 70, which emits IR light directed upward toward the user's lower body. The IR illumination can advantageously provide therapeutic exposure to the quadriceps, hamstrings, and/or calves, providing targeted circulation enhancement in the primary muscle groups engaged in the squat movement. The IR light may further illuminate the hip flexors and gluteal muscles, assisting with muscle relaxation and metabolic stimulation, as well as the core stabilizers of the lower torso, which may aid in postural support and endurance.

In the configuration of FIG. 4B, the resistance band support tubes 35 are oriented in an active, upright position, allowing for direct force transmission from the resistance bands 80 to the resistance bar 40. The distal openings at the upper portion of the tubes 35 can allow the resistance bands 80 to extend freely while maintaining alignment with the user's squat motion. Generally, the resistance bands 80 generate increasing resistance as the user 5 ascends from the squat position, facilitating a progressive overload training effect. The resistance band support tubes 35 are mounted to the base 20 in a pivotable engagement, allowing for resistance angle adjustments based on user preference and training intensity. For squatting exercises, the user 5 may grip the forward-biased handles 42, promoting secure control of the bar 40 during the squat motion.

Figure 4C:
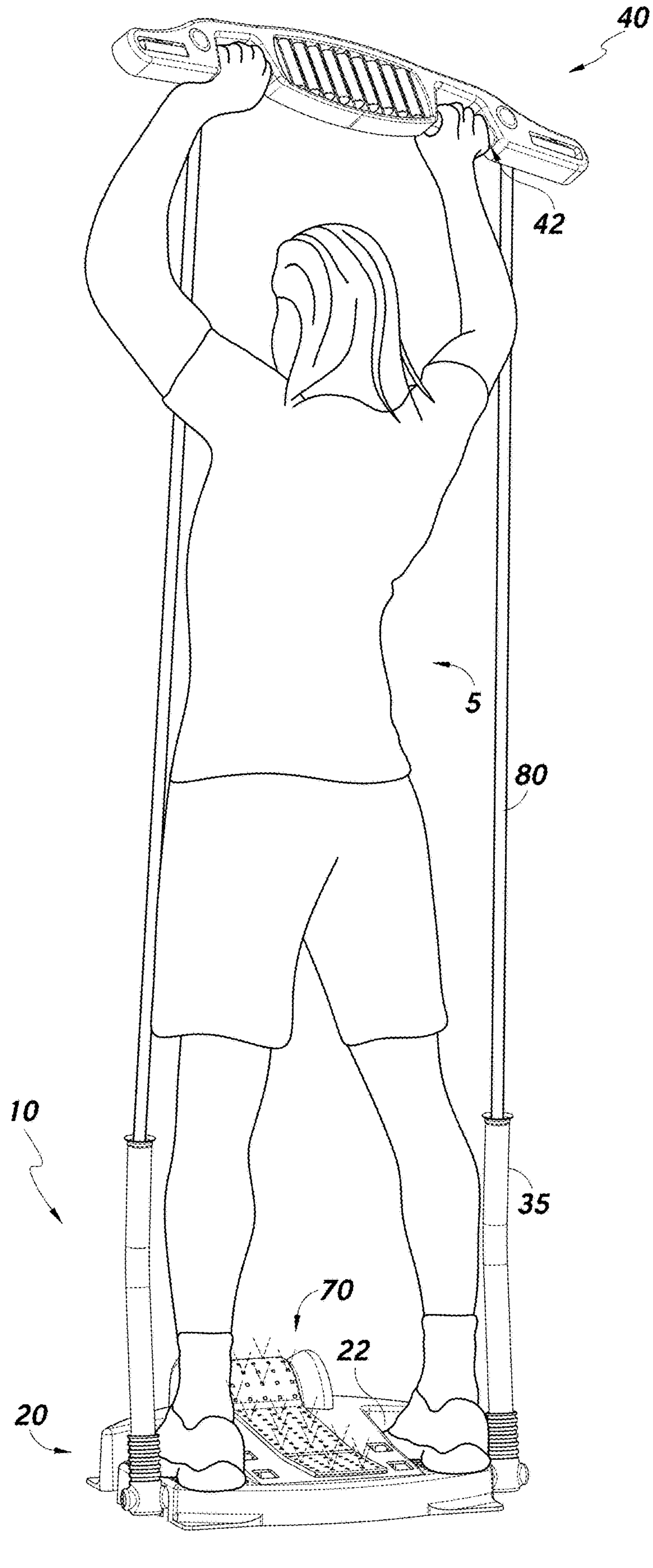
FIG. 4C shows a user engaged in an overhead press-type resistance exercise while utilizing an infrared-integrated, multi-functional training system in accordance with one or more embodiments.

FIG. 4C shows a user 5 engaged in an overhead press-type resistance exercise while utilizing the infrared-integrated, multi-functional training system 10. The user 5 is shown standing upright on the foot platforms 22 with a stable, shoulder-width stance. In the depicted action, the resistance bar 40 is gripped by the user's hands at the handles 42 and is being raised above the head in an overhead press movement. In the process of such exercise, the elbows may be fully extended as the bar reaches its highest position, aligning the arms with the user's vertical axis. The resistance bands 80 are tensioned as they extend from the distal openings of the resistance band support tubes 35, providing progressive resistance loading as the bar is elevated.

The base 20 includes the integrated infrared (IR) light strip 70, which emits infrared light directed upward toward the user's lower body. In a lift exercise like that shown in FIG. 4B, the IR illumination can provide illumination/therapy for the quadriceps, hamstrings, and/or calves, which can promote muscle relaxation and circulation improvement. The IR light may further illuminate the core stabilizing muscles of the lower torso, which can promote postural engagement and fatigue reduction. Additionally, the hip flexors and gluteal muscles may be illuminated, supporting joint mobility and flexibility.

In the illustrated exercise, the resistance band support tubes 35 are in an upright position, allowing for desirable force transmission from the resistance bands 80 to the resistance bar 40. The distal openings at the upper portion of the tubes 35 allow the resistance bands 80 to extend freely, accommodating the full range of motion of the overhead press movement. In performing the illustrated exercise, the resistance bar 40 may be positioned in front of the user's torso before being raised overhead in a controlled motion. The user 5 can grip the forward-biased handles 42, allowing for proper wrist alignment and effective force transmission.

Figure 5:
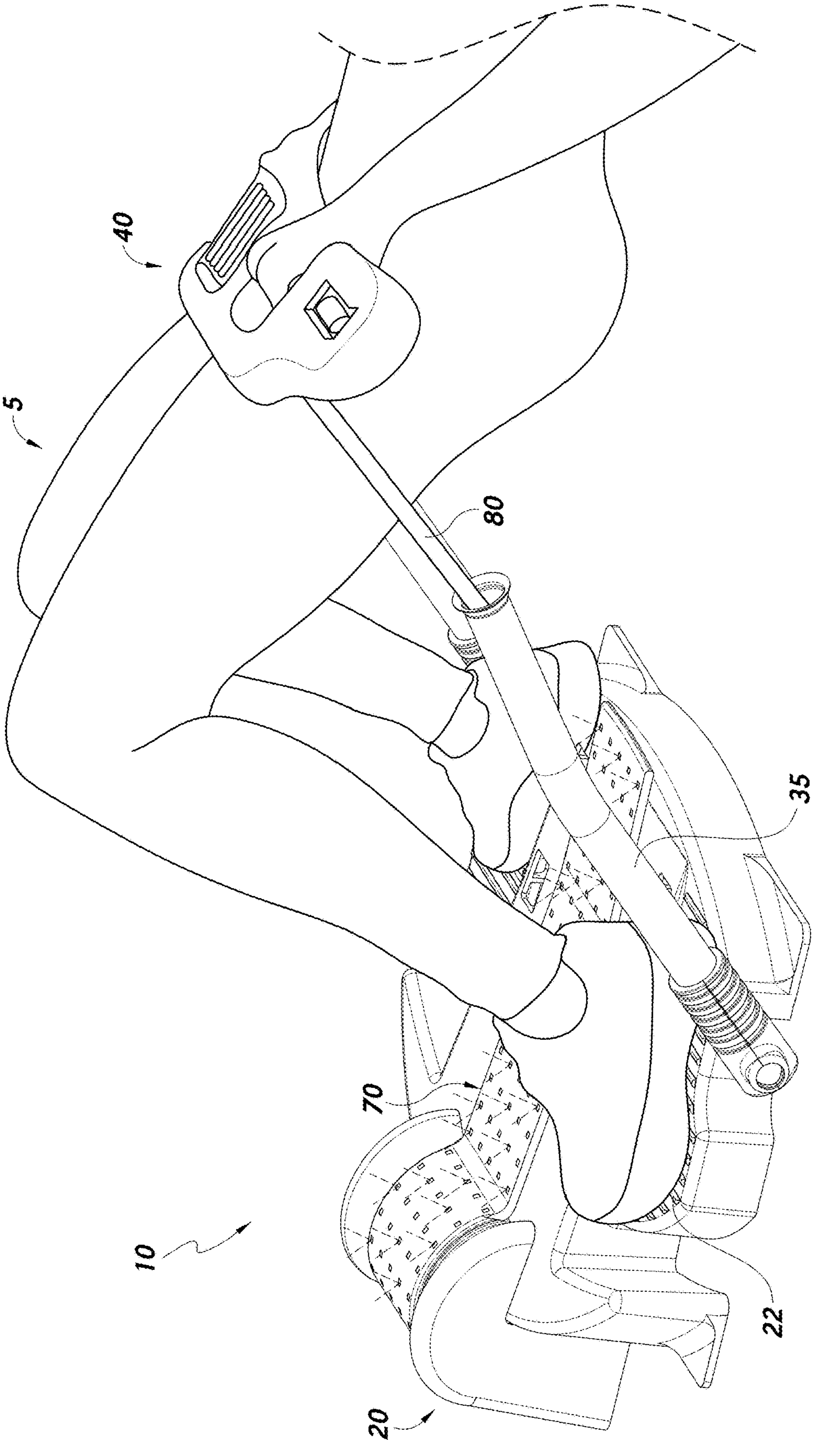
FIG. 5 shows a user engaged in a glute bridge-type resistance exercise utilizing an infrared-integrated, multi-functional training system in accordance with one or more embodiments.

FIG. 5 shows a user 5 engaged in a glute bridge-type resistance exercise utilizing the infrared-integrated, multi-functional training system 10. The user 5 is shown lying supine on a flat surface in front of the base 20 of the training system 10. The user's feet may be planted firmly on the foot platforms 22, with the knees bent at an angle to facilitate hip extension movement. The resistance bar 40 is shown positioned across the user's upper quadriceps, hip crease, and/or groin area, acting as a counterforce to the resistance bands 80. In the figure, the user 5 is shown actively engaging in a hip thrust or glute bridge motion, lifting the pelvis upward against the tensile force of the resistance bands 80.

The infrared (IR) light strip 70 integrated with the base 20 can emit IR light directed upward toward the user's lower body. For example, in connection with the illustrated exercise, the IR illumination can provide therapeutic exposure to the inner thighs, hip adductors, and/or surrounding musculature, which can advantageously aid in circulation and muscular activation. The IR lighting may further illuminate the gluteal muscles, hamstrings, and/or core stabilizers, which can promote recovery, flexibility, and enhanced blood flow. The pelvic and hip flexor regions may further be illuminated, potentially improving mobility and reducing muscle tightness.

The resistance band support tubes 35 are shown rotated forward, aligning the distal openings in a directional path toward the user's upper thighs. This forward-angled tube orientation can allow for effective force transmission, facilitating the application of a downward and posterior force vector by the bar 40 and resistance bands 80 against the user's lifting motion. The resistance bands 80 extend from the support tube openings and attach to the resistance bar 40. The pivot-mounting of the resistance band support tubes 35 can allow for manipulation to a controlled angle of resistance, promoting optimal muscle loading and preventing excessive lateral deviation.

Figure 6:
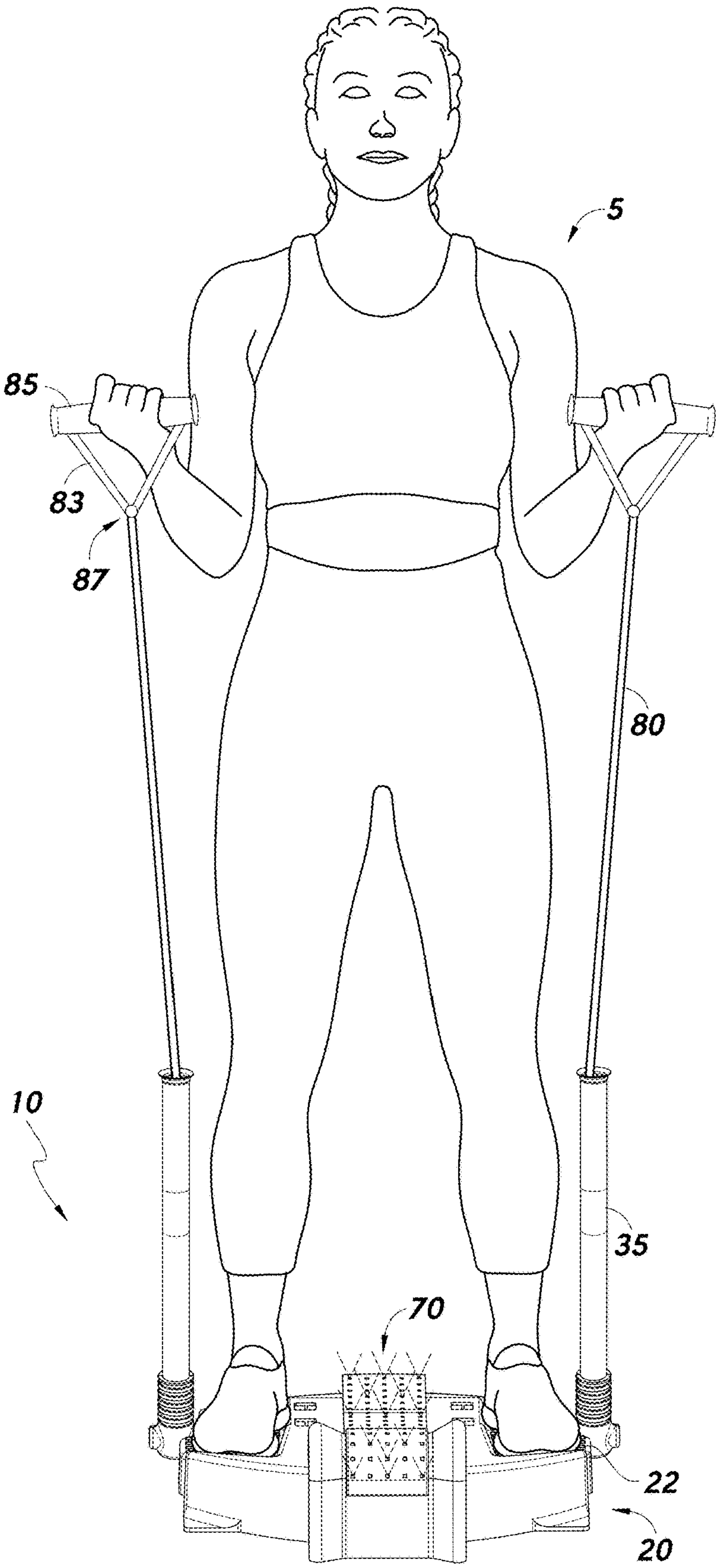
FIG. 6 shows a user engaged in a unilateral arm curl resistance exercise while utilizing infrared therapy using a multi-functional training system in accordance with one or more embodiments.

FIG. 6 shows a user 5 engaged in a unilateral arm curl resistance exercise while utilizing infrared (IR) therapy using the multi-functional training system 10. In the illustrated configuration, the resistance bar 40 has been removed, and resistance band handles 81 are attached directly to the distal ends of the resistance bands 80, allowing for independent arm movement with resistance from the bands 80.

In the depicted exercise, the user 5 is standing erect on the foot platforms 22, facing forward in a balanced position with a shoulder-width stance to promote stability during the exercise. The individual resistance band handles 81 are connected to the resistance bands 80, allowing the user to perform independent arm curls with resistance. The user 5 can grip the resistance band handles 81 with each hand (or a single hand), palms facing forward/upward in a supinated position, and lift one or both hands upward toward the shoulders in a curling motion. As the user raises the handles 81, the resistance bands 80 stretch, creating progressive resistance loading as the arms move through the curl motion.

The IR lighting 70 integrated with the base 20 can emit infrared light directed upward toward the user's lower body to provide therapeutic exposure to the inner thighs, groin region, and lower torso, which can improve circulation and flexibility. In addition, the IR lighting 70 can illuminate the hip adductors and stabilizing muscles, which can support muscle activation and blood flow during standing exercises. The calves and lower leg muscles can also be illuminated during the illustrated exercise, promoting increased circulation and potential metabolic stimulation.

When performing the depicted exercise, the resistance band support tubes 35 can be positioned in an upright position, ensuring proper resistance band alignment for direct force transmission to the user's arms. The user 5 can grip the individual resistance band handles 81, which can be attached to the resistance bands 80 via a secure, quick-connect locking mechanism 87. The handles 81 may have a triangular shape with a foam-covered, straight grip bar 85 for wrist and hand comfort. Corded side segments 83 can extend from both ends of the grip bar 85, forming a triangular profile that converges at the attachment point 87 with the resistance bands 80.

Figure 7:
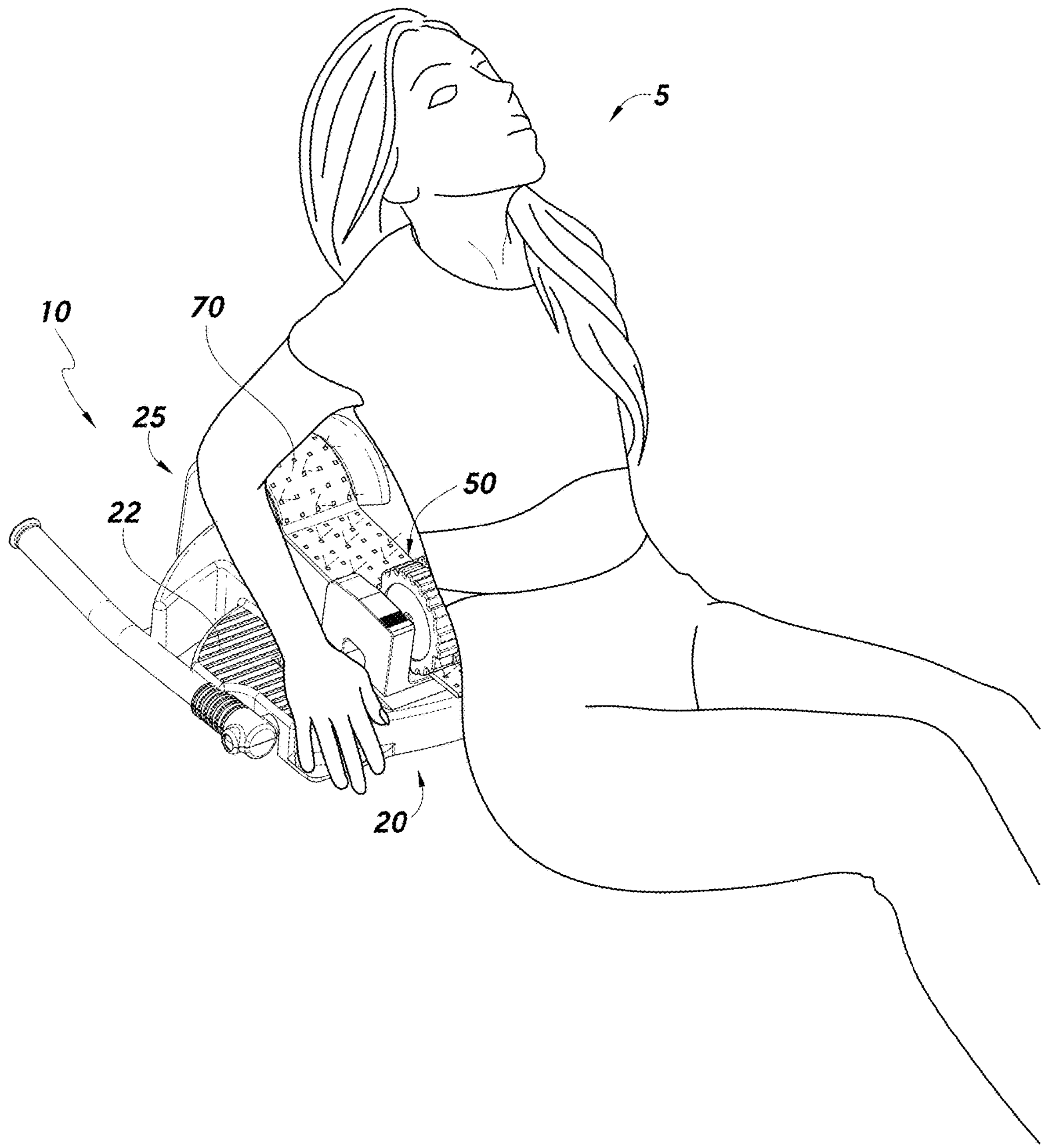
FIG. 7 shows a user engaged in a lumbar therapy exercise utilizing an infrared-integrated, multi-functional training system in accordance with one or more embodiments.

FIG. 7 shows a user 5 engaged in a lumbar therapy exercise utilizing the infrared-integrated, multi-functional training system 10. In the illustrated configuration, the lumbar therapy wheel 50 is mounted to the anterior aspect of the back support platform 26, allowing the user 5 to perform controlled rolling movements against the wheel 50 for spinal therapy and massage benefits. The user 5 is shown seated on a surface in front of the training system 10, facing away from the base 20. The user's lower back may be positioned against the lumbar therapy wheel 50, which is securely mounted on the front of the back support platform 26. The user can lean back into the wheel 50, applying controlled body weight pressure to facilitate rolling movement along the lumbar spine, for example. In performing such exercise, the user 5 may support her upper body by placing hands on the foot platforms 22, which can help provide stability for controlled movement during the rolling therapy session.

The back-support surface 26 and the headrest support 25 can include portions of the IR light strip 70, which emit IR light directed upward and rearward toward the user's upper body. The IR illumination can provide therapeutic exposure to the lower and upper back, lumbar spine, and shoulders, promoting muscle relaxation and circulation enhancement. The neck and head may also be exposed to illumination in the illustrated position, which can provide targeted IR therapy to the cervical spine, scalp, and surrounding tissues.

The lumbar therapy wheel 50 is rotatably mounted on the front surface of the back support platform 26, allowing for smooth rolling motion. The wheel 50 may be constructed from a durable, cushioned material, such as comprising high-density foam, textured rubber coating, and/or the like. The mounting mechanism of the wheel 50 can include a secure docking system that allows for removable or adjustable positioning based on user preference, as well as a rotational axle or bearing system to enable fluid, friction-minimized rolling movement. In some embodiments, the wheel assembly 50 includes resistance control features (e.g., variable friction settings) to modify the rolling experience. When performing the illustrated exercise, the resistance band support tubes 35 can be rotated backward, positioning them in a low-profile, stowed orientation so as to prevent interference with the user's arms and upper body movements.

Figure 8:
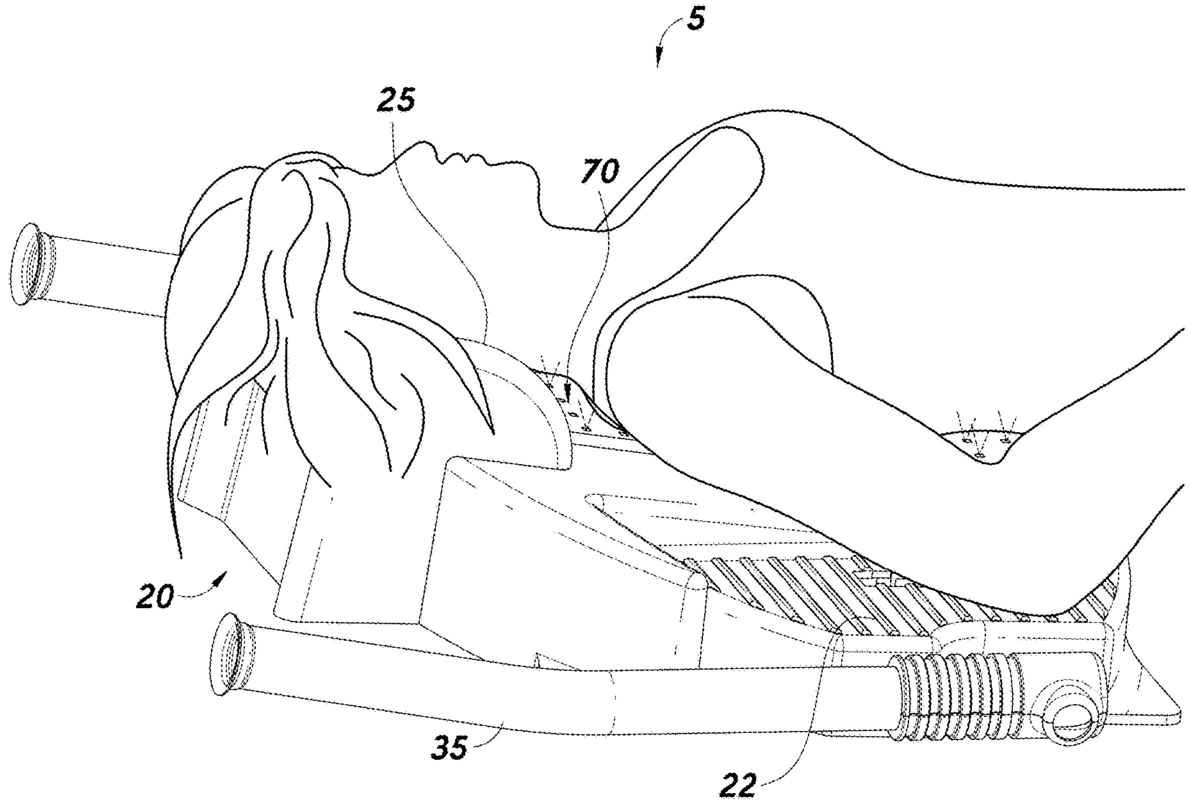
FIG. 8 shows a user lying in a reclined position on the base of an infrared-integrated multi-functional training system in accordance with one or more embodiments.

FIG. 8 shows a user 5 lying in a reclined position on the base 20 of the infrared-integrated multi-functional training system 10. In the illustrated position, the user 5 may utilize the system's integrated infrared (IR) light therapy for muscle recovery and relaxation. When used in such a manner, the resistance band tubes 35 of the system 10 may be lowered to the ground for unobstructed arm positioning, while the IR light strip 70 emit targeted illumination onto the user's back, neck, and/or head.

The user 5 is shown lying supine on the back support platform 26, with her head resting on the headrest support 25. The user's elbows can be positioned on the foot platforms 22, allowing for a relaxed and open upper-body posture. The user's spine, shoulders, and neck are fully supported by the contoured/angles back-support surface 26, providing effective anatomical alignment for passive therapy. The back-support surface 26 and/or headrest 25 can include integrated IR light sources of the lighting 70, which emit infrared light directed upward against the user's upper body. For example, the lighting 70 may illuminate the thoracic and/or lumbar spine, potentially enhancing circulation and muscular relaxation in the back. The user's shoulders may further be illuminated, reducing muscle stiffness and tension accumulation. The illustrated position/configuration can further provide therapeutic illumination of the neck, head, and/or scalp, potentially improving blood flow to the cervical spine, alleviating postural fatigue, and/or providing neural relaxation.

Figure 9A:
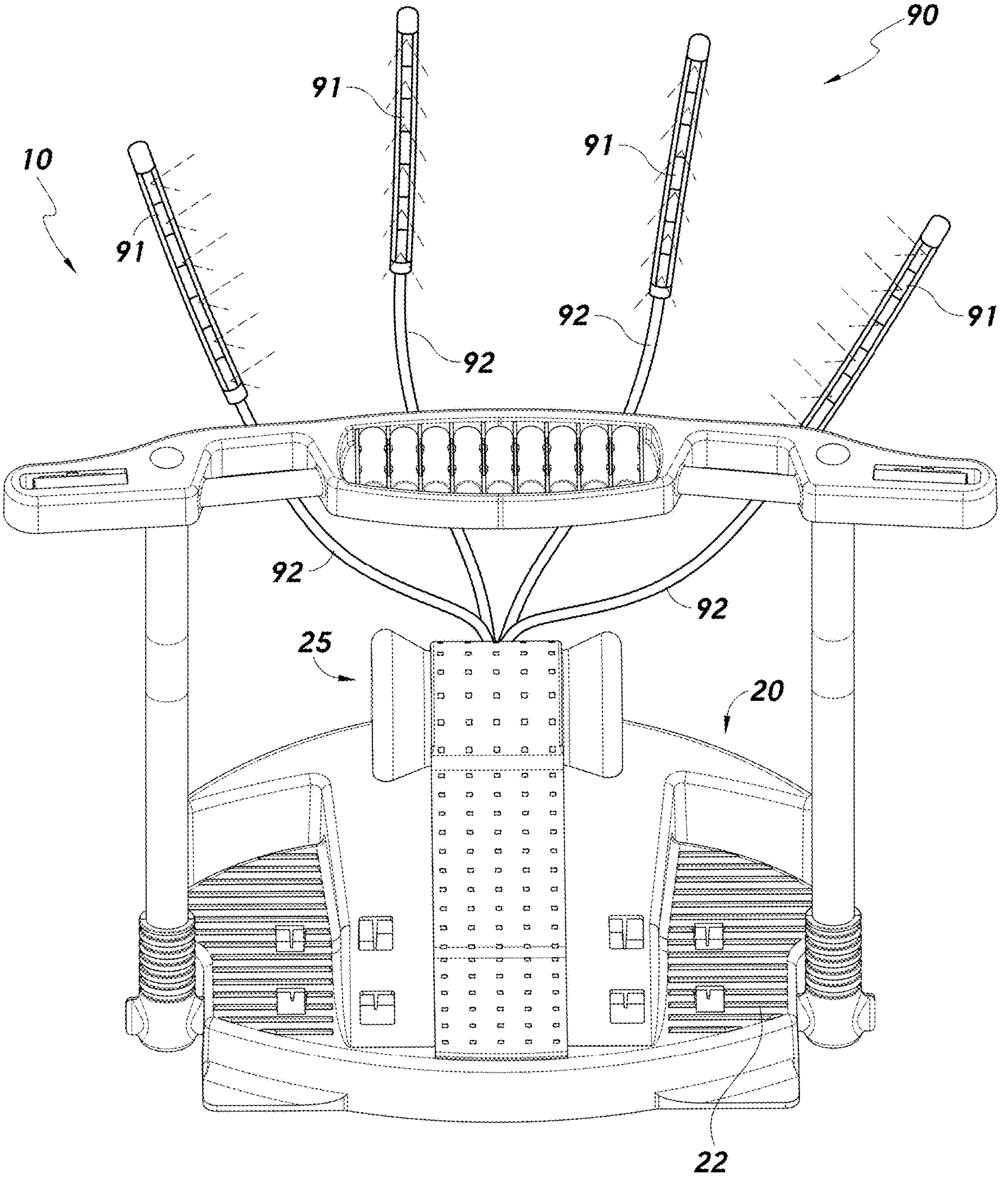
FIG. 9A shows an infrared-integrated exercise system implemented with a resistance bar and incorporating a set of infrared lighting arms in accordance with one or more embodiments.

FIG. 9A shows the infrared-integrated exercise system 10 implemented with a resistance bar 40 and incorporating a set of infrared (IR) lighting arms 90 which may extend from the posterior aspect of the base 20, near the headrest 25, or from any other portion of the base 20. These configurable IR lighting arms 90 are positionable in multiple orientations, enabling directed infrared therapy towards the central exercise region where the user would typically stand, perform resistance training, or engage in passive therapy sessions.

As with other examples disclosed herein, the exercise system 10 includes a stable base 20 with a back-support surface 26, foot platforms 22, and a headrest 25. The foot platforms 22 are positioned at the anterior aspect of the base 20, providing stable footing for standing-based resistance exercises. The resistance bar 40 is coupled to resistance bands (not shown), which extend through the resistance band support tubes 35. In some embodiments, the resistance bands do not extend through the tubes 35, but rather are fixed to distal ends of the tubes/shafts 35 at their proximal base.

The system 10 can include any number of lighting arms 90, such as four (4) IR lighting arms 90, as shown. The IR lighting arms 90 can be elongate, flexible members extending from the posterior aspect of the base 20. The IR lighting arms 90 can emanate outward in a distributed manner, radiating IR light toward the central exercise region when positioned as shown in FIG. 9A. Each IR lighting arm 90 may include an adjustable, shape-retaining structure, allowing the arms to be repositioned at various angles and orientations such that they remain in the manipulated shape/configuration after manual adjustment.

The distal portions of the IR lighting arms 90 include infrared light strips 91 that emit directed IR illumination. Each light strip 91 can extend approximately 6 inches to 1 foot along the distal end of each IR arm 90, providing broad illumination coverage. In some examples, the IR light strips 91 radiate infrared wavelengths in the range of approximately 850 nm to 940 nm, optimizing deep-tissue therapeutic benefits. The IR arms 90 incorporate shape-memory or adjustable tensioning mechanisms, allowing for dynamic repositioning to optimize IR exposure for different user activities. For example, the arms 90 may be configured/positioned in multiple orientations, including an upward-angled position for upper-body therapy when performing standing resistance exercises, a horizontal position to provide side-angled illumination for full-body therapy, a forward-directed position directing IR light toward the anterior region of the system, such as for facial, neck, and upper-body IR exposure, and/or any other desired position/configuration. Each IR lighting arm 90 may include a support shaft 92 that supports the light strip 91. The support shaft 92 may comprise individual pivoting joints or friction-based locks, allowing for secure positioning at user-selected angles/shapes. The configurable IR arms 90 can enable customized light positioning based on the user's height, stance, and exercise mode. The support shaft 92 may be considered a shape-memory shaft/member in that when it is manipulated to a certain shape, it may be include/biased to remain in the defined shape after removal of the users hand or other shaping force.

Figure 9B:
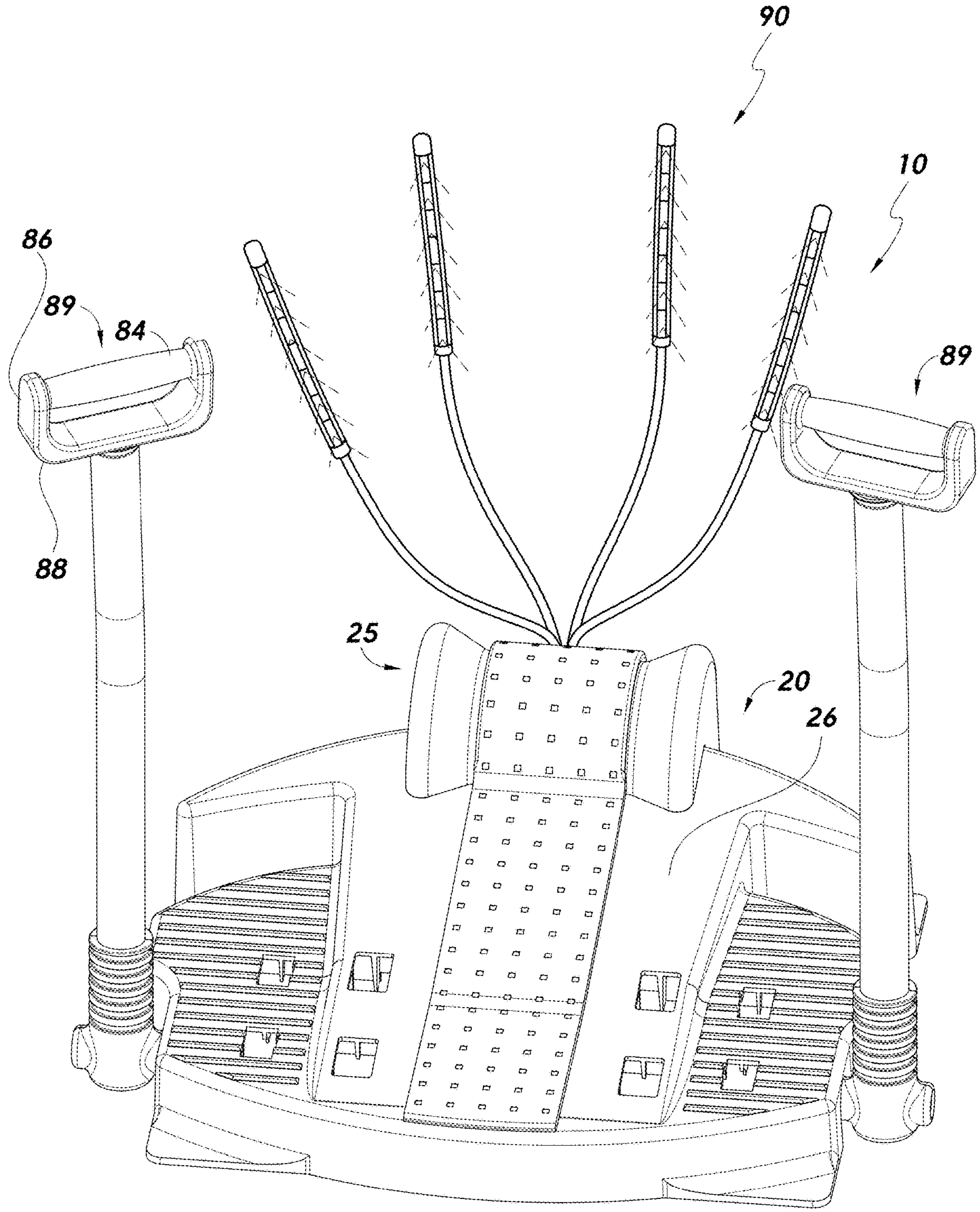
FIG. 9B shows an infrared-integrated multi-functional training system with resistance band handles in accordance with one or more embodiments.

FIG. 9B shows the infrared-integrated multi-functional training system 10 with the resistance bar removed, replaced by resistance band handles 89 positioned at the distal ends of the resistance band support tubes 35. The system retains its configurable infrared (IR) lighting arms 90, which emanate from the posterior aspect of the base 20 and project infrared illumination according to the implemented positioning/shaping of the IR arms 90.

Resistance band handles 89 have a different configuration than certain other examples shown and/or described in the present disclosure. For example, the handles 89 may have a rigid base 88 that are connected to the free ends of the resistance bands 80 and can rest on the distal ends of the resistance band support tubes 35. The handle base 88 may include side posts 86 that support the cross-bar handles 84. The absence of the resistance bar can enable greater freedom of movement, allowing unilateral and bilateral training options.

Figure 10A:
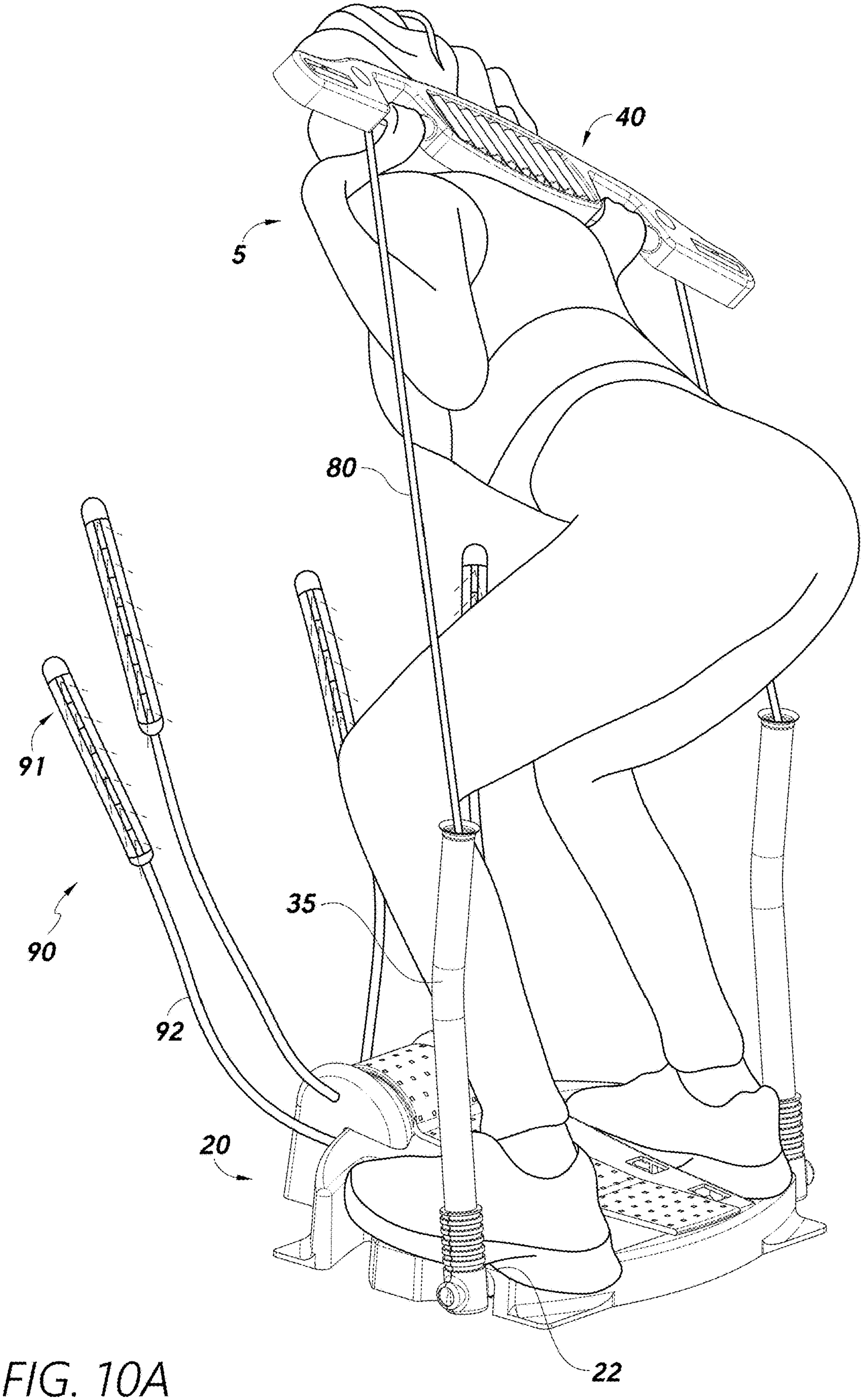
FIG. 10A shows a user engaged in a resistance exercise using an infrared-integrated training system in accordance with one or more embodiments.

FIG. 10A depicts a user 5 engaged in a resistance exercise with the resistance bar 40 positioned across the shoulders, resting against the back of the neck. The resistance bands 80 extend from the distal openings of the resistance band support tubes 35, providing progressive resistance as the user performs the movement. In this configuration, the infrared (IR) lighting arms 90 are positioned to project IR illumination toward the anterior side of the user's body. In the illustrated example, four IR lighting arms 90 extend from the posterior aspect of the base 20, radiating infrared light toward the user's chest, torso, and legs. FIG. 10A demonstrates the integration of forward-directed infrared therapy with resistance-based strength training, allowing for simultaneous active movement and therapeutic exposure.

Figure 10B:
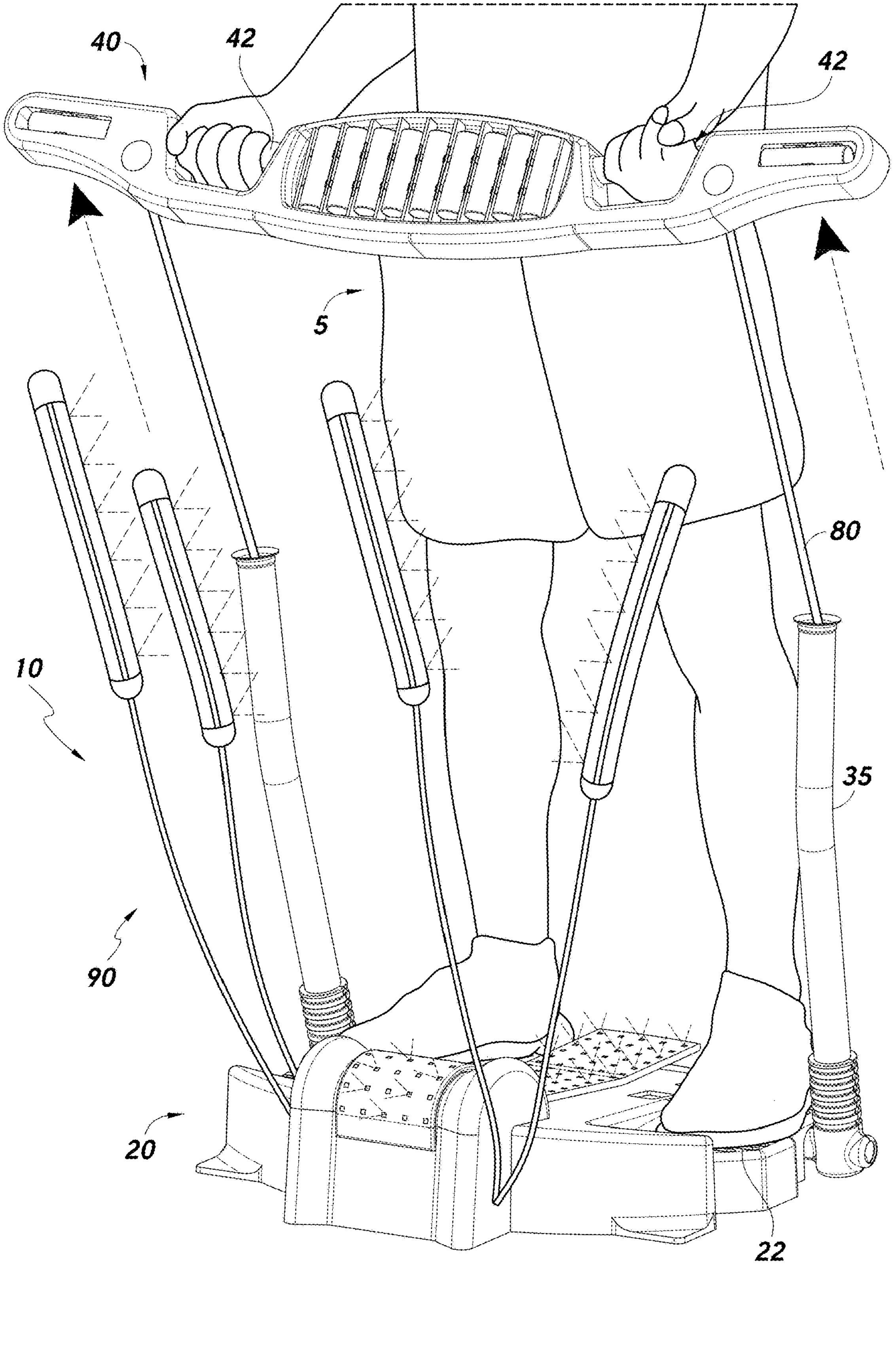
FIG. 10B shows a user engaged in a curl-type resistance exercise using a resistance bar of an infrared-integrated training system in accordance with one or more embodiments.

FIG. 10B shows a user 5 engaged in a curl-type resistance exercise using the resistance bar 40, which is gripped at the forward-biased handles 42 in front of the torso. The resistance bands 80 extend from the distal openings of the resistance band support tubes 35, providing progressive resistance as the user lifts the bar toward the upper chest. In this configuration, the infrared (IR) lighting arms 90 can be positioned to project infrared illumination toward the anterior side of the user's body. The IR lighting arms 90 can extend from the posterior aspect of the base 20, radiating light toward the user's chest, arms, and lower body. FIG. 10B demonstrates the integration of forward-directed infrared therapy with upper-body resistance training, enhancing muscle activation, circulation, and potential recovery benefits while performing dynamic strength exercises.

Figure 11B:
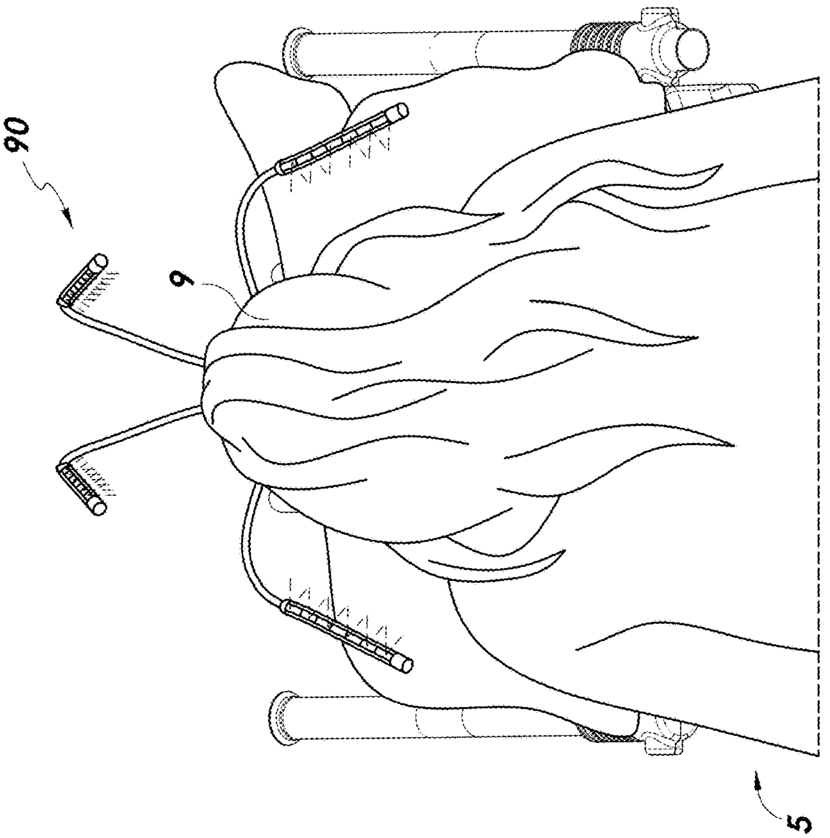
FIG. 11B shows a user in a prone position on an infrared-integrated multi-functional training system for therapy in accordance with one or more examples.
Figure 11A:
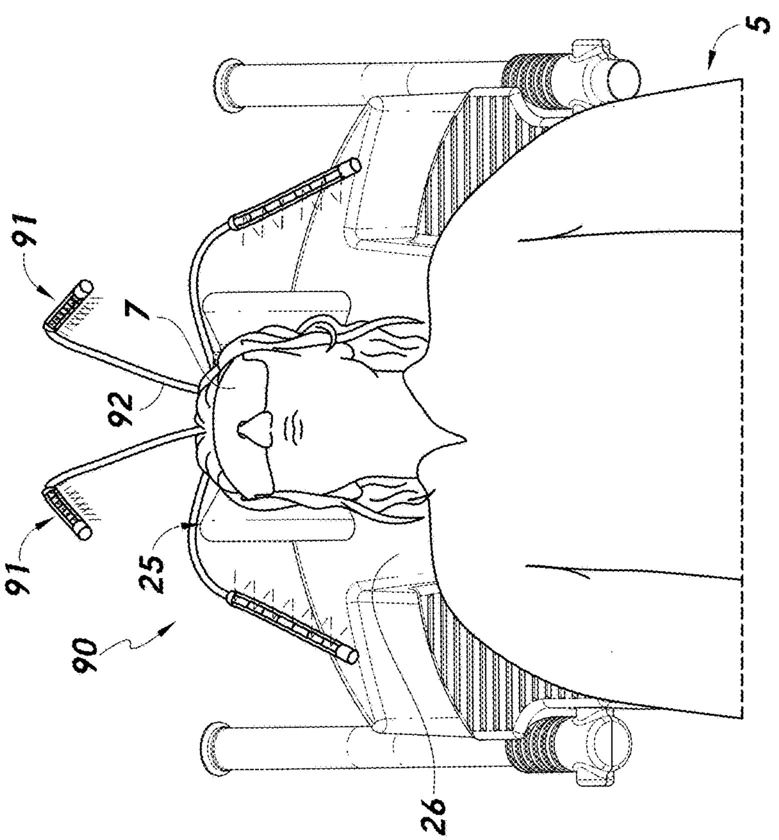
FIG. 11A shows a user lying in a reclined position on an infrared-integrated multi-functional training system for therapy in accordance with one or more embodiments.

FIG. 11A shows a user 5 lying in a reclined position on the infrared-integrated multi-functional training system 10, with the back positioned against the back support platform 26 and the head resting on the headrest 25. The infrared (IR) lighting arms 90 are adjusted into a forward-bent configuration, directing infrared illumination toward the user's face. The IR lighting arms 90 may extend from the posterior aspect of the base 20, near the headrest 25, with each arm 90 including an infrared light strip 91 at its distal end. The arms 92 are flexible and adjustable, allowing for multi-angle positioning to focus IR light onto specific regions of the user's body. In this configuration, the arms are oriented to converge IR light directly onto the user's facial region. IR lighting on the back-support surface 26 may further provide illumination on the head, neck and/or back of the user simultaneously with the facial therapy.

To ensure safe exposure to infrared light, the user 5 is shown wearing protective eyewear 7, which shields the eyes from potential overexposure while allowing the user to receive infrared therapy to the skin, muscles, and tissues of the face and upper neck. The eyewear 7 may be designed with infrared-blocking lenses or optical filters to prevent unwanted light penetration. FIG. 11A highlights the adjustability and targeted application of the IR lighting arms 90, demonstrating their capability to be positioned for direct facial therapy, which may be beneficial for facial circulation enhancement, relaxation, and potential therapeutic effects on the skin and underlying tissues.

FIG. 11B shows a user 5 lying face-down in a prone position on the infrared-integrated multi-functional training system 10, with the torso supported by the back support platform 26 and the head resting on the headrest 25. The infrared (IR) lighting arms 90 are positioned to direct infrared illumination onto the user's hair and the back of the head, enabling targeted infrared therapy for potential scalp and hair health benefits. For example, the IR lighting arms 90 can extend from the posterior aspect of the base 20, near a headrest structure/form, and feature infrared light strips positioned at their distal ends. The arms 90 can be flexible and adjustable, allowing for multi-angle positioning. In the illustrated configuration, the arms 90 are bent forward and downward to focus IR light directly onto the scalp and hair. FIG. 11B demonstrates the system's ability to provide directed infrared therapy for hair and scalp applications, which may stimulate circulation, promote follicular health, and support hair-strengthening benefits associated with IR exposure. The adjustable IR lighting arms 90 allow the light intensity and focus to be modified to suit user preferences and treatment needs.

Figure 12:
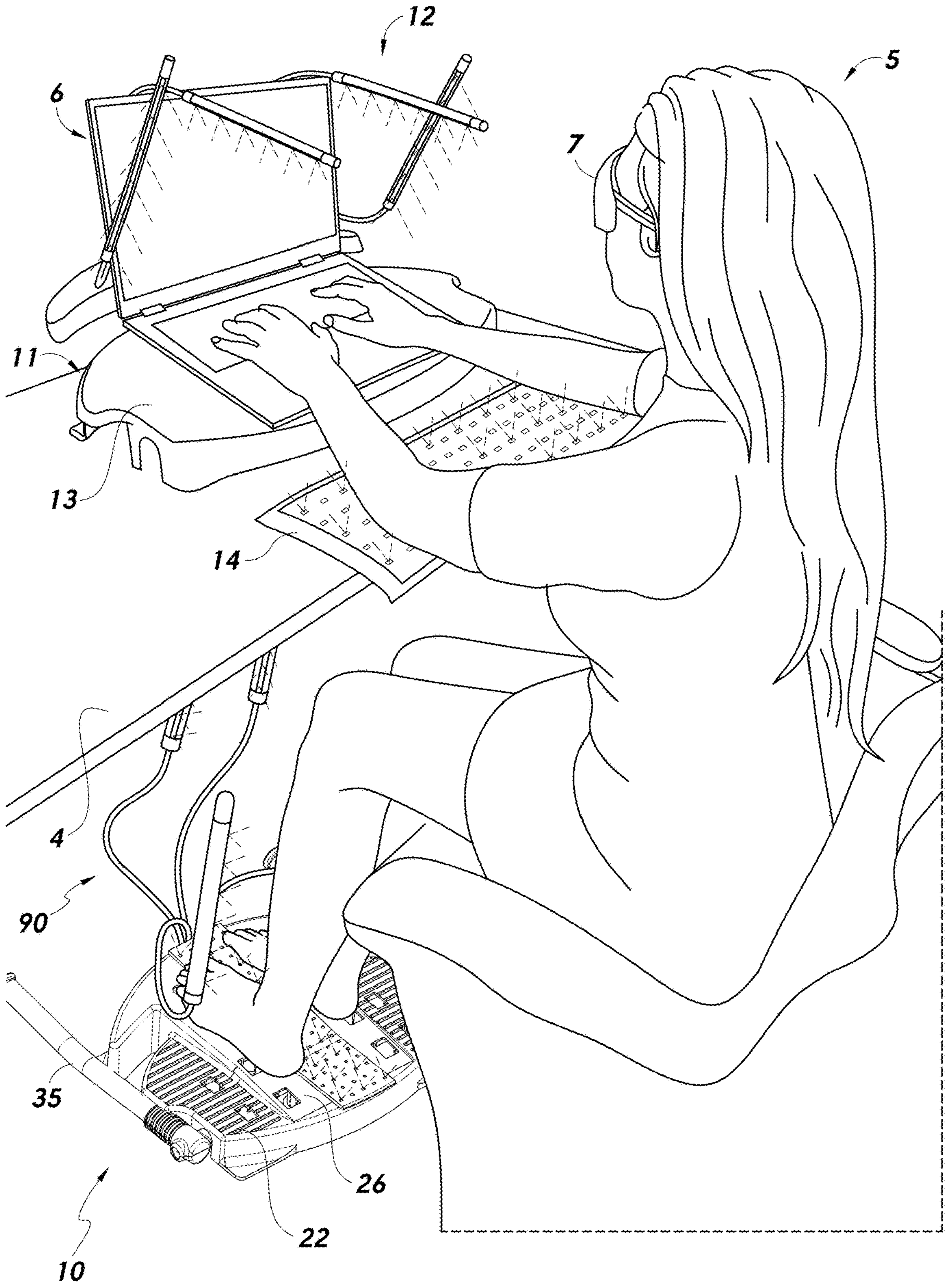
FIG. 12 depicts a user seated at a desk for infrared therapy using infrared-integrated systems in accordance with one or more embodiments.
Figure 13A:
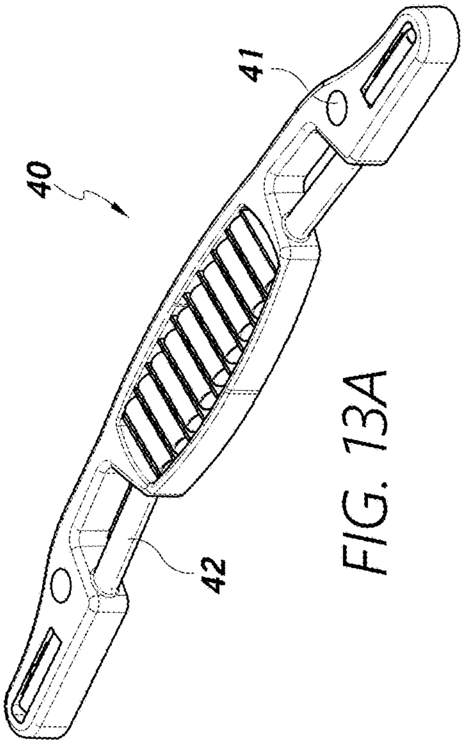
FIGS. 13A-13J show views of a resistance bar in accordance with one or more embodiments.
Figure 13B:
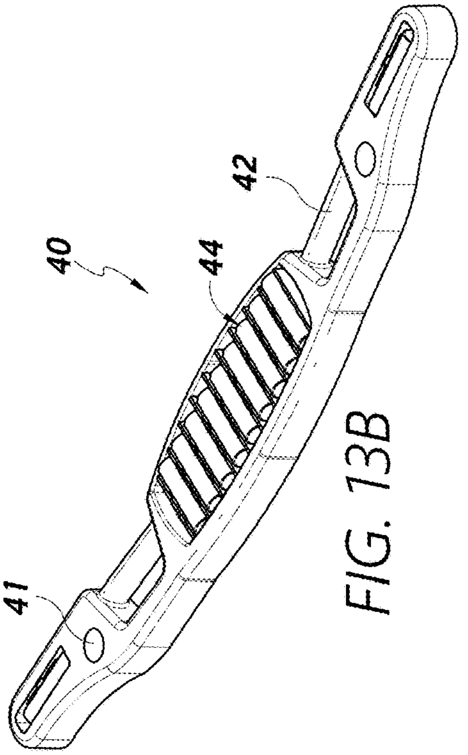
Figure 13C:
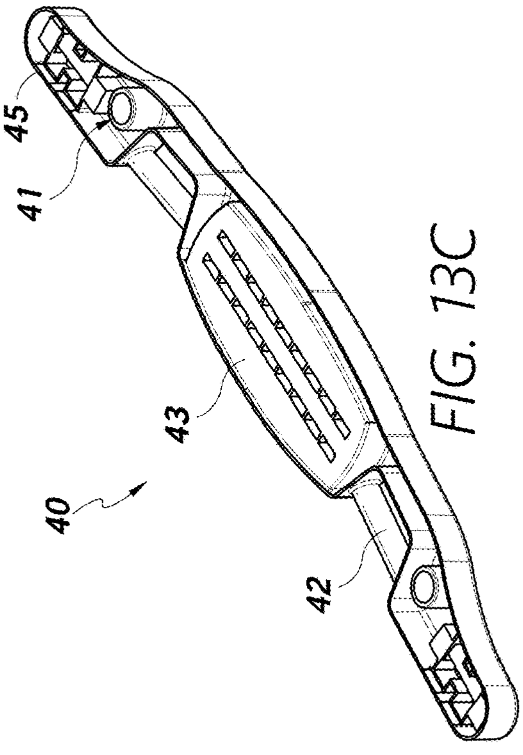
Figure 13D:
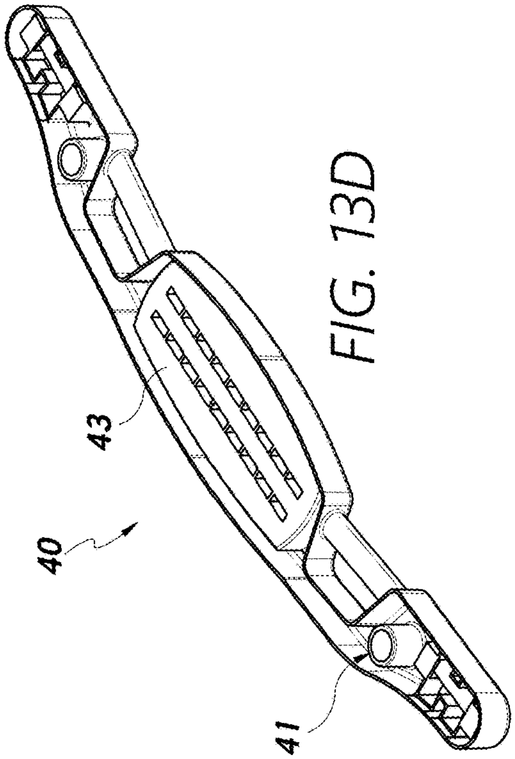
Figure 13E:
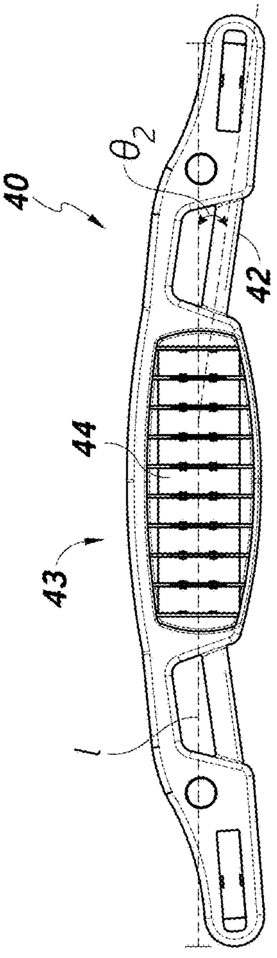
Figure 13F:
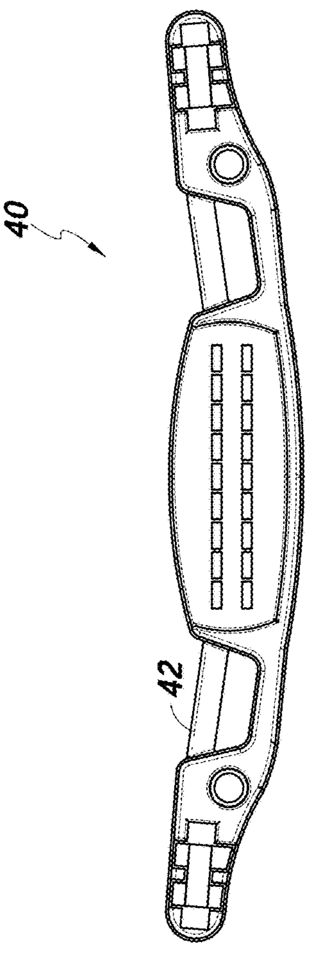
Figure 13G:
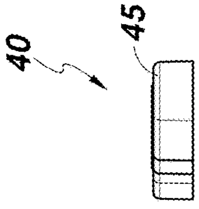
Figure 13H:
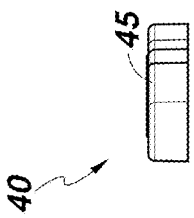
Figure 13I:
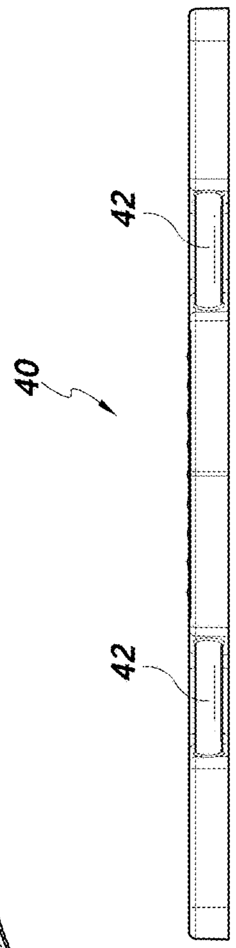
Figure 13J:
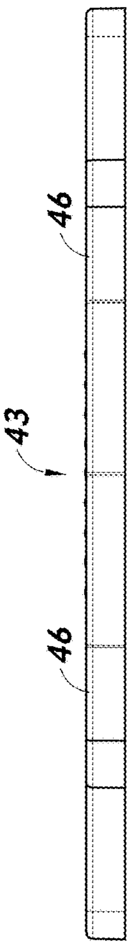

FIG. 12 depicts a user 5 seated at a desk 4, interacting with a laptop 6 placed on an infrared-equipped laptop support base 11. The multi-functional training system 10 is positioned underneath the desk 4, with the user's feet resting on the back support platform 26 or dedicated foot platforms 22. This configuration integrates infrared (IR) therapy for the lower body, upper body, and hands while enabling normal workstation activities such as typing.

The user 5 is shown in a seated position at the desk 4, with the feet placed on the back-support surface 26 of the training system 10. The infrared light strip 70 embedded within the back support platform 26 emits IR illumination directed upward, providing targeted therapy to the lower body, including the legs, thighs, and feet. The infrared lighting arms 90 of the training system 10 extend from the posterior aspect of the base 20 and are bent forward to project additional infrared illumination onto the user's lower body.

The user 5 is shown typing on the laptop 6, which is placed on a support surface 13 of the infrared-integrated laptop support base 11 positioned on the desk 4. The laptop support base 11 includes infrared light arms 12 extending from its rear side, positioned to project IR illumination toward the user's hands and forearms, extending around the laptop screen. The IR lighting arms 12 can be adjustable, allowing the emitted infrared light to be directed toward the user's wrists, hands, and forearms, providing therapeutic exposure while typing. The laptop support base 11 may also include integrated ergonomic elevation features to promote proper user posture and stable device positioning. In some implementations, an additional rectangular (or other-shaped) infrared light pad 14 is placed on the desk surface 4 beneath the user's elbows and forearms. The IR pad 14 can emit infrared illumination upward, providing exposure for the underside of the user's arms for enhanced circulation and muscle relaxation effects. This additional IR source can facilitate IR exposure for both the dorsal and palmar surfaces of the hands and forearms. Due to the multiple infrared light sources, the user 5 is shown wearing protective eyewear 7 designed to block excessive IR exposure to the eyes. The eyewear can promote safe engagement with the infrared therapy system while allowing the user to continue normal workstation activities without discomfort.

ADDITIONAL EMBODIMENTS

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "of" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A multi-functional exercise system comprising:

a base having a user-support top surface including:

- a back-support portion being angled and positioned at a lateral center of the base; and
- first and second foot platforms positioned on opposite lateral sides of the back-support portion;

a headrest form positioned adjacent to the back-support portion of the base;

an array of infrared (IR) lights including a first portion associated with the back-support portion of the base and a second portion associated with the headrest form;

a first resistance band tube positioned on a first lateral side of the base, the first resistance band tube having a first resistance band segment disposed at least partially therein and configured to extend out of a distal opening of the first resistance band tube; and a second resistance band tube positioned on a second lateral side of the base, the second resistance band tube having a second resistance band segment disposed at least partially therein and configured to extend out of a distal opening of the second resistance band tube.

2. The system of claim 1, wherein the first and second resistance band tubes are pivotably coupled to the base in a manner as to allow rotation of the first and second resistance band tubes between a stowed position at least partially substantially parallel with a bottom surface of the base and a raised position substantially perpendicular to the bottom surface of the base.

3. The system of claim 1, wherein a distal end of the first resistance band segment has a grip handle associated therewith.

4. The system of claim 3, wherein the grip handle has a grip handle base configured to support the grip handle on the distal opening of the first resistance band tube.

5. The system of claim 1, further comprising a resistance bar attached at a first end thereof to a distal end of the first resistance band segment and at a second end thereof to a distal end of the second resistance band segment.

6. The system of claim 5, wherein the resistance bar includes:

a first handle on a first lengthwise side of the resistance bar;

a second handle on a second lengthwise side of the resistance bar; and a first compartment for placement of removable weights positioned between the first handle and the second handle.

7. The system of claim 6, wherein the resistance bar further includes:

a first end portion lengthwise outside of the first handle and having a second weight compartment associated therewith; and a second end portion lengthwise outside of the second handle and having a third weight compartment associated therewith.

8. The system of claim 1, wherein each of the first and second foot platforms has a push-up handle dock associated therewith.

9. The system of claim 1, wherein the back-support portion of the base has a lumbar wheel removably mounted thereto.

10. The system of claim 1, further comprising a plurality of IR lighting arms that project from the base.

11. The system of claim 10, wherein:

each of the plurality of IR lighting arms includes a shape-memory adjustable shaft; and a light strip disposed along a lengthwise portion of the respective IR lighting arm.

12. The system of claim 1, wherein the headrest form has raised, tapered lateral sides.

13. The system of claim 1, wherein the array of IR lights is arranged in a rectangular grid that covers a center portion of the back-support portion and extends from a front of the back-support portion, to an end of the back-support portion, and over the headrest form.

* * * * *